(12) United States Patent
Richter et al.

(10) Patent No.: US 6,458,978 B1
(45) Date of Patent: Oct. 1, 2002

(54) FLUOROUS PHOSPHINES AND PROCESS FOR THEIR PREPARATION

(75) Inventors: Bodo Richter, Spremberg (DE); Aloysius Cornelius A. de Wolf, Utrecht (NL); Gerard van Koten, Den Dolder (NL); Berth Jan Deelman, Culemborg (NL)

(73) Assignee: Atofina Vlissingen B.V., Vlissingen (NL)

( * ) Notice: Subject to any disclaimer, the term of this patent is extended or adjusted under 35 U.S.C. 154(b) by 0 days.

(21) Appl. No.: 09/787,625

(22) PCT Filed: Sep. 29, 1999

(86) PCT No.: PCT/NL99/00603

§ 371 (c)(1),
(2), (4) Date: May 21, 2001

(87) PCT Pub. No.: WO00/18774

PCT Pub. Date: Apr. 6, 2000

(30) Foreign Application Priority Data

Sep. 30, 1998 (EP) .............................................. 98203308

(51) Int. Cl.[7] .................................................. C07F 9/00
(52) U.S. Cl. ........................... 556/14; 556/13; 556/404; 502/162
(58) Field of Search ............................... 568/13, 16, 17; 556/13, 14, 18, 21, 404; 502/162, 165, 166

(56) References Cited

U.S. PATENT DOCUMENTS 2,673,210 A    3/1954   Frisch et al.
5,045,302 A  * 9/1991   Kelly et al.

FOREIGN PATENT DOCUMENTS

EP    0 633 062 A1    1/1995
WO    WO 98/32533    7/1998

OTHER PUBLICATIONS

CA:115:680118 abs of Z. Anorg. Allg. Chem by Grobe et al 592 pp. 121–40 1991.*
CA:114:229128 abs of Z. Anorg. Allg. Chem by Grobe et al 590 pp. 65–80 1990.*
Alvey, Luke, J., et al., "Additions of PH3 to Monosubstituted Alkenes of the Formula $H_2C-CH(CH_2)_x(CF_2)_yCF_3$: Convenient, Multigram Syntheses of a Family of Partially Fluorinated Trialkylphosphines with Modulated Electronic Properties and Fluorous Phase Affinites," *J. Org. Chem.*, 63(18): 6302–6308 (1988).
Guillevic, Marie–Andrée, et al., "Synthesis, Structure, and Oxidative Additions of a Fluorous Analogue of Vaska's Complex, trans–$[IrCl(CO)\{P[CH_2 CH_2(CF_2)_5CF_3]_3\}_2]$–Altered Reactivity in Fluorocarbons and Implications for Catalysis," Angew. *Chem. Int. Ed. Engl.*, 36(15):1612–1615 (1997).
"Alternative ligands. XXX. Novel tripod ligands XM' $(OCH_2PMe_2)_n(CH_2CH_2Pme_2)_{3-n}$ (M'=Si, Ge; n= 0–3) for cage structures," *Chemical Abstracts*, 120 (15):1059 (1994).

* cited by examiner

*Primary Examiner*—Jean F. Vollano
(74) *Attorney, Agent, or Firm*—Hoffmann & Baron, LLP

(57) ABSTRACT

A fluorous phosphine wherein the phosphor is coupled to at least one aryl or alkyl moiety, to which moiety a fluorous tail is coupled, wherein a spacer group, containing a non-carbon atom, is positioned between the aryl or alkyl moiety and the fluorous tail, a process for the preparation of said phosphines, metalcomplexes, catalysts and catalyst compounds therefrom and their use in catalysis.

23 Claims, 6 Drawing Sheets

(m = 1, 2, 3; x = 6, 8)

US 6,458,978 B1

FLUOROUS PHOSPHINES AND PROCESS FOR THEIR PREPARATION

This application is the U.S. National Phase of International Application Number PCT/NL99/00603 filed on Sep. 29, 1999.

BACKGROUND OF THE INVENTION

The invention relates to fluorous phosphines and a process for their preparation. The invention also relates to the metal complexes based on the fluorous phosphines, methods for the preparation of metal complexes, to catalysts based on the fluorous phosphines and the use of said catalysts in catalysis.

In catalysis, homogeneous catalytic systems are often preferred over heterogeneous ones because of their better product and substrate selectivity. A general problem in homogeneous catalysis, however, is separation and recycling of the catalyst. This has led to the development of several supported catalytic systems, e.g. immobilised versions of homogeneous catalysts on inorganic supports (M. G. L. Petrucci, A. K. Kakkar, Adv. Mater., 1996, 8, 251 and references cited therein, W. A. Herrmann, B. Cornils, Angew. Chem. Int. Ed. Engl, 1997, 36, 1098 and references cited therein) and systems connected to polymers or dendrimers (J. W. Knapen, A. W. Van der Made, J. C. Wilde, P. W. N. M. van Leeuwen, P. Wijkens, D. M. Grove, G. van Koten, Nature, 1994, 372, 659), with the combined advantages of both homogeneous and heterogeneous catalysis. Another elegant solution for this separation/recycling problem is the aqueous biphasic Ruhrchemie/Rhône-Poulenc process (W. A. Hermann, C. W. Kohlpaintner, Angew. Chem. Int. Ed. Engl., 1993, 32, 1524). In this process a water soluble version of the conventional Rh/PPh$_3$ catalyst is used, i.e. TPPTS/Rh (TPPTS=P(m-C$_5$H$_4$SO$_3$Na)$_3$). The catalytic process is performed under biphasic conditions with the aqueous phase containing the catalyst, and the organic phase containing the products. The catalyst can be easily removed from the products by phase separation. In this process losses of rhodium are kept below $10^{-6}$ mg/kg of product produced.

Despite the advantage of aqueous biphasic systems in catalysis, they also have some disadvantages. Some reactants or catalysts hydrolyze when exposed to water, resulting in decreased performance for these systems. Furthermore, due to the two phase nature of the system, the catalyst is not homogeneously mixed with the products. Therefore, the reactants or catalysts have to cross or react at the phase boundary which could lead to mass flow limitations, resulting in considerable lower reaction rates as compared to single phase homogeneous systems. This effect is enhanced by the often low solubility in water of organic substrates with higher molecular weights (I. T. Horváth, J. Rábai, Science, 1994, 266, 72).

The special physical properties of perfluorinated compounds and the problem associated with aqueous bi-phasic catalysis inspired Horváth et al. to use fluorous bi-phase systems in rhodium catalysed hydroformylation (I. T. Horváth, J. Rábai, Science, 1994, 266, 72). Here, the fluorous phase, as an alternative to aqueous phase, denotes a solvent, which is rich in C—F bonds. Below a certain temperature the fluorous phase does not mix with an organic phase containing the reactants and products. At a certain temperature, the system consists of a fluorous phase, containing a fluorous phase soluble catalyst, and a hydrocarbon phase, containing the reactants. Above this temperature, the two phases mix to form one phase allowing efficient homogeneous catalysis to proceed. Catalyst recovery and product separation can then be achieved by cooling of the reaction mixture below the temperature where phase separation occurs. Alternatively, if e.g. the phase transition temperature of a certain fluorous bi-phasic system is too high, or if desirable for other reasons, the catalytic reaction can also be performed under bi-phasic conditions.

For reactions which cannot be performed in an aqueous bi-phasic system, e.g. due to low solubility of reactants in the aqueous layer, diffusion limitations or water sensitive components a fluorous bi-phasic system could be an alternative. Perfluoro solvents do not usually mix with water and can contain water only on the ppm level (see D. W. Zhu, Synthesis, 1993, 953).

To render a catalyst preferentially soluble in a fluorous phase, it is usually functionalised with one or several perfluoroalkylgroups, also sometimes referred to as ponytails or pigtails. Most often, perfluorohexyl (C$_6$F$_{13}$) and perfluoro-octyl (C$_8$H$_{17}$) groups are being used. The length and the number of perfluoroalkylgroups are important because they influence the solubility of perfluoralkylated compounds in a fluorous solvent.

Usually the reactivity and selectivity of homogenous catalysts are modified by reacting the catalytically active metal with different coordinating ligands. A widely used class of ligands for these purposes are phosphines. A serious drawback of the use of perfluorinated ponytails in ligands in general are the strong electron withdrawing properties of perfluoroalkyl functions. These properties can influence the coordinating characteristics of the phosphor atom and hence the resulting catalytic activity dramatically.

In order to reduce undesired effects of the perfluorinated ponytails on the activity of the catalyst, spacers have been introduced. The spacers which have been developed so far comprise ethylene, propylene or substituted phenyl, such as for instance described in I. T. Horváth, J. Rábai, Science, 1994, 266, 72; European Patent application 94-304877.7, U.S. Pat. No. 9,388,706; Bhattacharya, D. Gudmundsen, E. G Hope, R. D. W Kemmit, D. R. Paige. A. M. Stuart, J. Chem. Soc. Perkin Trans. I, 1997, 3609; J. J. J Juliette, I. T. Horváth, J. A. Gladysz, Angew. Chem. Int. Ed. Engl, 1997, 36, 161; S. Kainz, D. Koch, W. Baumann, W. Leitner, Angew. Chem. Int. Ed. Engl, 1997, 36, 1628.

However, there continues to be a need for more variations of these spacers for a more delicate tuning of ligands also because the existing catalyst systems with fluorous ligands often have lower activity when compared with their non-fluorous counterparts or analogues.

It is therefore a goal of the present invention to provide for fluorous ligands with different spacer groups. It is a further goal of the invention to provide for ligands with spacers which can reduce or even nullify the effect of the perfluorinated ponytails of the ligand on the catalytic activity. It is another goal of the present invention to overcome the above-mentioned disadvantages of other approaches and to provide for ligands who will allow efficient product-catalyst separation when applied in catalysis

SUMMARY OF THE INVENTION

It has now been found that the use of certain non-carbon fragments in the spacer results in ligands that further enhance the applicability of the ponytail tailored ligands and of catalysts based thereon for use in homogeneous catalysis.

Accordingly, the invention relates to a fluorous phosphine wherein at least one phosphor atom is coupled to at least one aryl or alkyl moiety, to which moiety a fluorous tail is coupled, wherein a spacer group, containing a non-carbon atom, is positioned between the aryl or alkyl moiety and the fluorous tail.

DETAILED DESCRIPTION OF THE INVENTION

Figure 1:
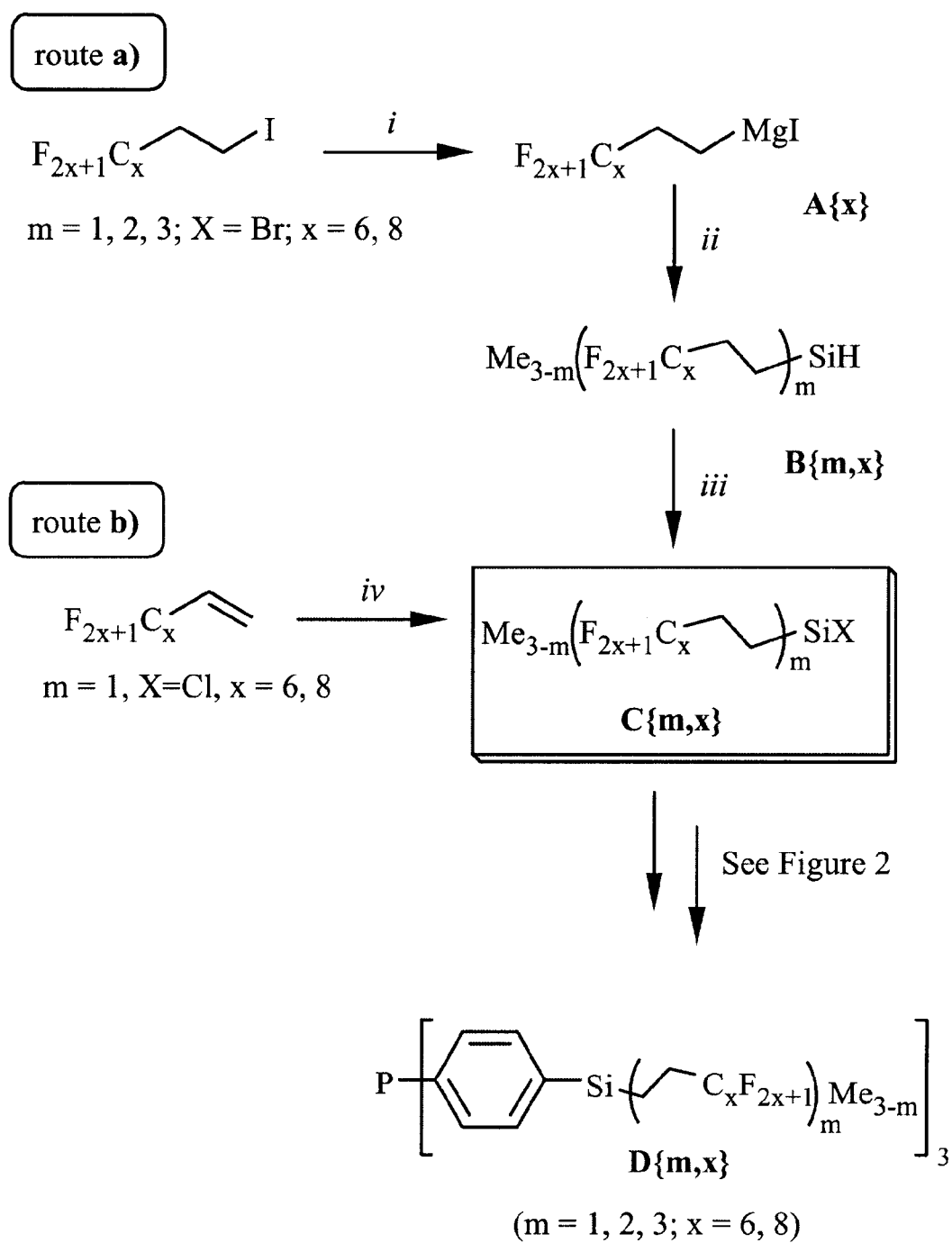
FIG. 1. Reagents: (i) 1.5 HSiMe$_2$Cl, catalyst: H$_2$PtCl$_6$ (aq); (ii) Excess of Mg; (iii) HSi (Me$_{3-m}$)Cl$_m$; (iv) Br$_2$.

The invention is a fluorous phosphine wherein at least one phosphor atom is coupled to at least one aryl or alkyl moiety. A fluorous tail is coupled to the aryl or alkyl moiety, and a spacer group, containing a non-carbon atom, is positioned between the aryl or alkyl moiety and the fluorous tail.

The phosphines that in general can be most finely tuned with respect to their steric and electronic properties are monophosphines and diphosphines. By varying the delicate tuning of the ligands, the activity and selectivity of the catalyst containing these phosphines can be significantly improved. Accordingly, a preferred embodiment provides for fluorous mono- and/or diphosphines.

In a more preferred embodiment, the phosphines according to the invention can be depicted by their general structure, P—A—S—T, wherein P is phosphorous, A is the alkyl or aryl moiety, S is the spacer, containing a non-carbon atom and T is the fluorous tail.

A preferred embodiment of the invention concerns fluorous phosphines and fluorous diphosphines wherein the fluorous tail is a C$_x$F$_{2x+1}$ perfluoroalkyl group, wherein x is an integer from 1 to 30.

In a preferred embodiment of the invention the alkyl or aryl moiety is optionally substituted alkyl or aryl, preferably optionally substituted phenyl.

It is possible for the alkyl or aryl moiety to carry, additional to the phosphor and the non-carbon substituent, other substituents. There are, in general, no limitations to these substituents. These substituents can for instance be selected from other or identical ponytails, more spacer-extended ponytails, simple substituents which are considered common substituents in the design of ligands for homogenous catalysis such as for instance the substituents described by Tolman et al. in Chemical Reviews 1977, 77, pp 313 or C. D. Frohming and Ch. W. Kohlpainter in "Applied Homogenous Catalysis with Organometallic compounds, B. Cornil, W. A. Hermann (Eds.), VCH, Weinheim 1996, Vol. 1, pp 29–104.

In an embodiment of the invention the spacer group in the fluorous phosphines is

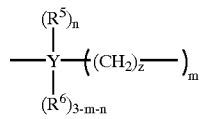

wherein Y is Si, Sn or Ge; m is an integer from 1 to 3; R$^5$, R$^6$ is —C$_1$–C$_{14}$-(cyclo)alkyl, —C$_1$–C$_{14}$-aryl, —C$_1$–C$_{14}$-ar(cyclo)alkyl, —C$_1$–C$_{14}$-(cyclo)alkylaryl, and/or, if m is not equal to 3, fluorous tails; n is an integer from 0 to 3, the sum of m and n is smaller than or equal to 3 and z is an integer from 0 to 10. The branching point Y can thus be used to attach up to 3 perfluoroalkyl tails, in that way allowing the synthesis of phosphines with high fluorine content.

Without being bound by theory it is assumed that the presence of a non-carbon atom such as Si, Sn or Ge is capable of neutralising and/or compensating the electron-withdrawing effect of the fluorous ponytails on the phosphor of the ligand. This will effectively minimise the possible electron-withdrawing effects of the ponytails on the metal and thus on the catalytic activity.

A preferred embodiment of the invention is therefore a fluorous phosphine wherein the spacer contains a moiety that neutralises the electron-withdrawing effect from the fluorous tail.

A preferred embodiment of the invention relates to a fluorous monophosphine of the formula P(R$^1$) (R$^2$) (R$^3$), wherein at least one of the groups R$^1$, R$^2$ and R$^3$ is alkyl-R$^4$ or optionally substituted aryl-R$^4$ and wherein R$^4$ is the spacer group coupled to the fluorous tail.

Another embodiment of the invention relates to a fluorous diphosphine of the formula (R$^1$) (R$^2$) P—Z—P(R$^3$) (R$^7$), wherein Z is a achiral or chiral bridging hydrocarbyl moiety and wherein at least one of the groups R$^1$, R$^2$, R$^3$ or R$^7$ is alkyl-R$^4$ or optionally substituted aryl-R$^4$ and wherein R$^4$ is the spacer group coupled to the fluorous tail.

A preferred embodiment of the invention is a fluorous monophosphine wherein any one of R$^1$, R$^2$, R$^3$, is optionally substituted aryl-R$^4$ or a fluorous diphosphine wherein any one of R$^1$, R$^2$, R$^3$, or R$^7$ is optionally substituted aryl-R$^4$.

A preferred embodiment of the invention is a fluorous phosphine wherein Y is Si.

A preferred embodiment of the invention is a fluorous phosphine wherein R$^5$ and/or R$^6$ is preferably —C$_1$–C$_6$-alkyl, more preferably ethyl or methyl, most preferably methyl.

A preferred embodiment of the invention is a fluorous diphosphine wherein Z is —(CH$_2$)$_q$— with q is an integer from 1 to 10.

The invention also relates to a process for the preparation of fluorous phosphines of formula P(R$^1$) (R$^2$) (R$^3$) comprising steps (a)–(c) or (d), followed either by steps (e)–(g) or step (h), with steps (a)–(h) being defined as:

a) metallating X (CH$_2$)$_z$C$_x$F$_{2x+1}$;
b) Reacting the metallated product obtained in step (a) with HY (X)$_m$(R$^5$)$_n$(R$^6$)$_{3-m-n}$;
c) Reacting the compound obtained in step (b) with X$_2$;
d) Reacting CH$_2$=CH (CH$_2$)$_z$C$_x$F$_{2x+1}$ with HY (X)$_m$(R$^5$)$_n$ (R$^6$)$_{3-m-n}$;
e) Mono-metallating an optionally substituted dihaloaryl compound ArX$_2$ and reacting this compound with the compound obtained through steps (a)–(c) or d;
f) Metallating the compound obtained in step (e);
g) Reacting the metallated compound obtained in step (f) with a trivalent phosphorus compound containing one or more P—X' bonds;

h) Reacting the compound obtained through steps (a)–(c) or (d) with tri-metallated phosphine obtained from P(ArX)$_3$ by halogen metal-exchange;

wherein X is halogen or pseudohalogen, X' is halogen, pseudohalogen, alkoxy, aryloxy, amido, triphlato or aryl leaving group, preferably Cl, OMe, OEt, NMe$_2$ or NEt$_2$, and Ar is aryl.

Throughout this description the different compounds are labeled using the designation A{m,x}–K{m,x}. Here, m signifies the number of fluoro tails per silicon centre whereas x represents the number of fluorine-bearing carbon atoms in the C$_x$F$_{2x+1}$ fluoro tails. Thus D{2,6} denotes a phosphine as depicted in FIG. 1, with m is 2 and x is 6 resulting in P[C$_6$H$_4$Si(CH$_2$CH$_2$C$_6$F$_{13}$)$_2$Me-4]$_3$. The compounds D{0} and G{0} depict species P(C$_6$H$_4$SiMe$_3$-4)$_3$ and (Me$_3$SiC$_6$H$_4$-4)$_2$PCH$_2$CH$_2$P(C$_6$H$_4$SiMe$_3$-4)$_2$ which serve as non-fluorous reference compounds.

Figure 2:
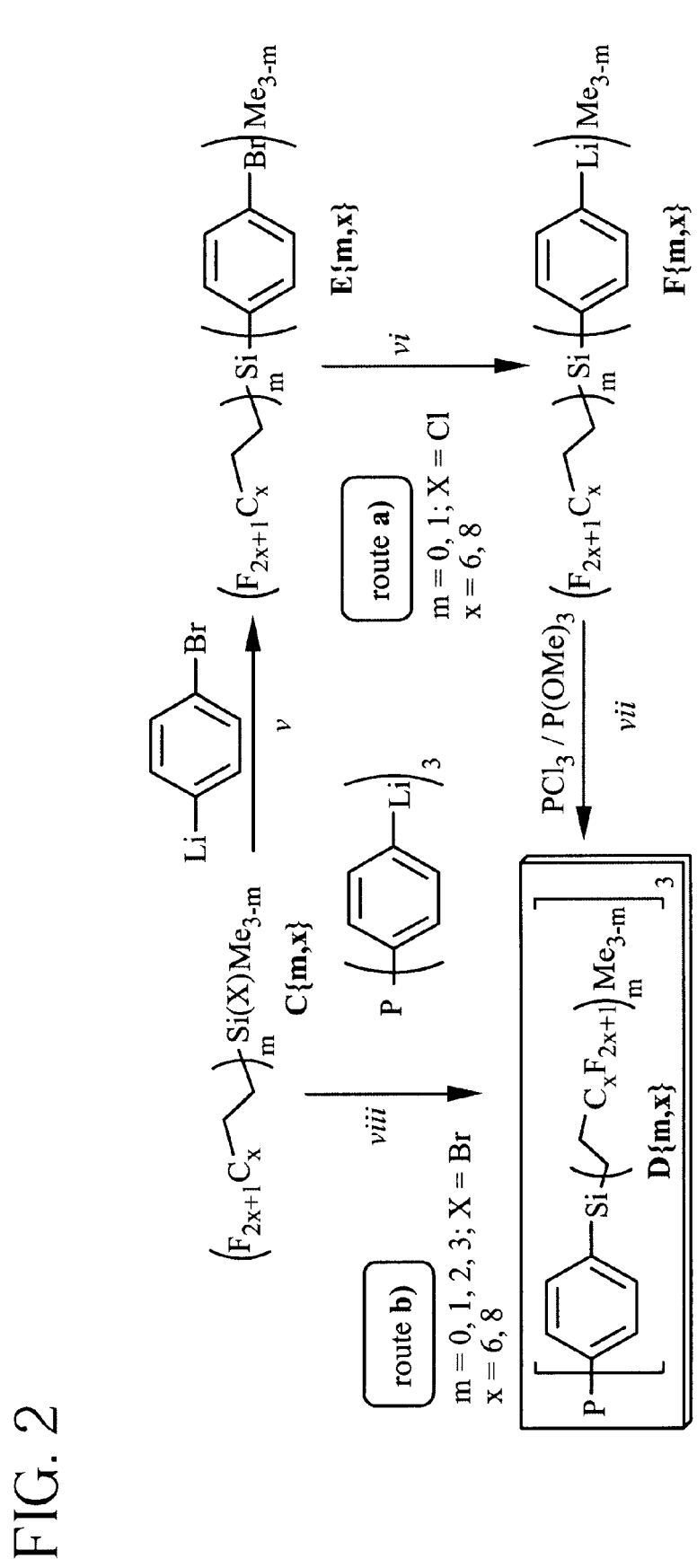
FIG. 2. Reagents: (v) 1,4-Li C$_6$H$_4$Br from 1,4-BrC$_6$H$_4$Br and n-BuLi or from 1,4-I C$_6$H$_4$Br and 2 $^t$BuLi; (vi) $^n$BuLi or 2 $^t$BuLi; (vii) PCl$_3$ or P(OMe); (viii) P(C$_6$H$_4$-p-Li)$_3$ from P(C$_6$H$_4$-p-Br)$_3$ and 6 $^t$BuLi.

For preferred embodiments of the invention these synthetic procedures are further clarified by FIGS. 1 and 2.

The invention also relates to a process for the preparation of fluorous diphosphines of formula (R$^4$Ar)$_2$P—Z—P(ArR$^4$)$_2$ comprising the following steps:

a) Reacting (X')$_2$P—Z—P(X')$_2$ with mono metallated ArX$_2$;

b) Metallating compound (XAr)$_2$P—Z—P(ArX)$_2$ obtained in step (a);

c) Reacting the compound obtained in (b) with R$^4$X;

wherein Z is a bridging hydrocarbyl moiety, X is halogen, X' is halogen, pseudo halogen, alkoxy, aryloxy, amido, triphlato or aryl leaving group, preferably Cl, OMe, OEt, NMe$_2$ or NEt$_2$, and R$^4$ is the spacer group coupled to the fluorous tail.

The metallation procedures in the process according to the invention are conventional metallation procedures such as Grignard formation, lithiation with organolithium reagents such as butyllithium, whether n-, sec- or tert- or transmetallation reactions, for instance with Zn, Na, K or Cs compounds.

Figure 3:
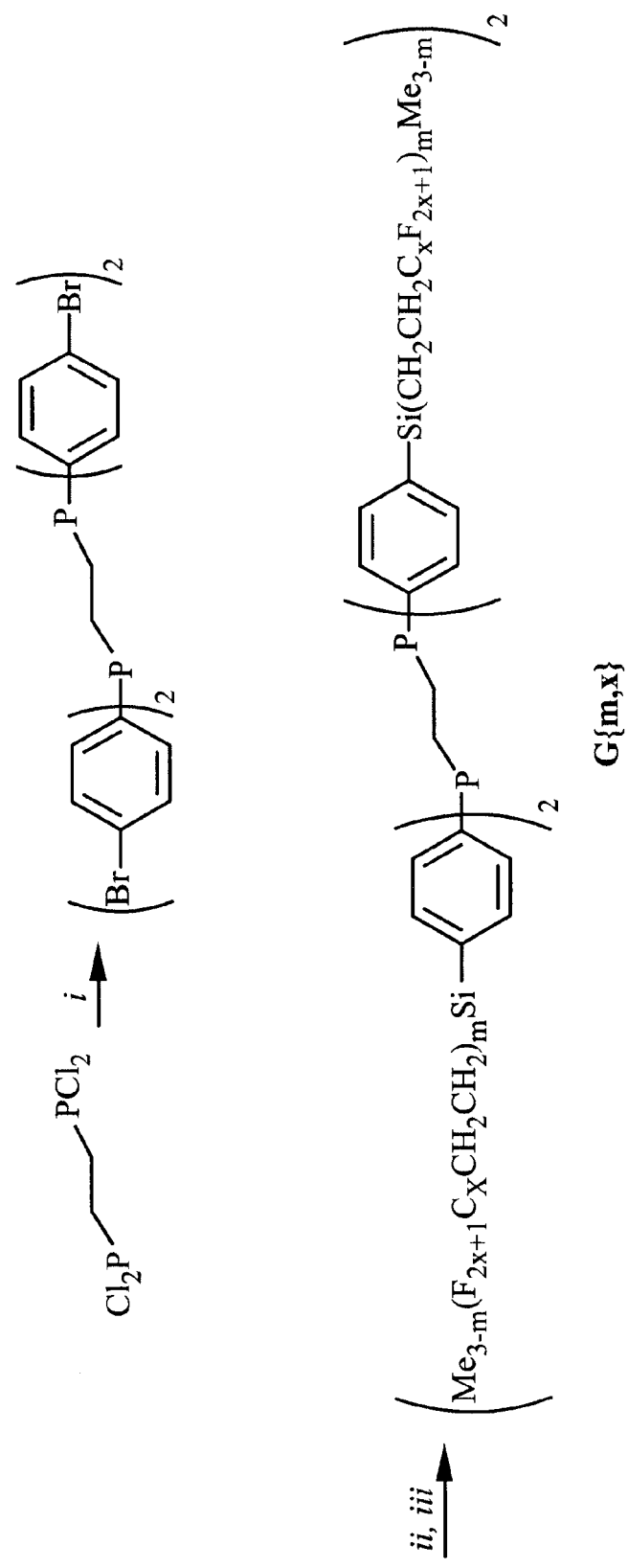
FIG. 3. Reagents: (i) 4 p-BrC$_6$H$_4$Li; (ii) 8 $^t$BuLi; (iii) 4 XSi (CH$_2$CH$_2$C$_x$F$_{2x+1}$)$_m$Me$_{3-m}$ (m=0, 1; X=Cl, m=2, 3; X=Br)

For preferred embodiments of the invention these synthetic procedures are further clarified by FIG. 3.

As these ligands are likely candidates for use in homogenous catalysis, the invention in another aspect relates to a metalcomplex comprising at least one of the fluorous phosphines. In an embodiment of the invention, the metal in the metal-phosphine complex as described is selected from rhodium, platinum, palladium, nickel, iron, ruthenium, osmium, cobalt, or iridium, preferably from rhodium, platinum, palladium, or nickel.

In an another embodiment of the invention, a metalcomplex, comprising a metal and at least one fluorous phosphine, is a catalyst or catalyst compound and the invention accordingly relates to catalytic systems comprising these catalysts or catalyst compounds for carrying out homogeneous catalytic reactions. More specific, the catalysts according to the invention can be used in chemical reactions wherein the chemical reaction is hydroformylation, hydroboration, hydrosilylation, carbonylation, Heck-type reactions, oligo- and polymerisations, cross-coupling and hydrogenation of unsaturated compounds, preferably alkenes.

Solubility and Phase Distribution of the Fluorous Monophosphines and Diphosphines The invention provides the use of the monophosphine and diphosphine ligands developed for fluor phase immobilization of homogeneous catalysts, the solubility behaviour of the fluorous phosphines themselves in different fluorous and non-fluorous solvents and fluorous bi-phasic solvent combinations was studied. To demonstrate the increased fluorphase affinity the solubilities of the monophosphines D{m,x} in organic and fluoro-solvents were determined and listed in Table 1 as the amount of solute dissolved in 1 L of pure solvent.

Without being bound by theory, it appears that the "like dissolves like" principle is valid. The fluorous phosphines have consistently higher solubilities in the fluorous solvent c-C$_6$F$_{11}$CF$_3$ than in non-fluorous n-octane. There appears to exist an optimum in the fluorocarbon solubility for m=2 (0.25–0.28 mol/L). For m=3 the solubility drops to values below 0.17 mol/L).

TABLE 1

Solubilities of Fluorous Triaryl Monophosphines D{m,x} in Organic and Fluorous Solvents at 25° C., Expressed as the Amount of Phosphine which Dissolves in 1 L of Pure Solvent.

| Compound | F content (wt %) | n-octane (mol/L) | n-octane (g/L) | c-C$_6$F$_{11}$CF$_3$ (mol/L) | c-C$_6$F$_{11}$CF$_3$ (g/L) |
|---|---|---|---|---|---|
| D{1,6} | 50 | 0.037 | 55 | 0.050 | 74 |
| D{1,8} | 55 | 0.008 | 14$^a$ | 0.055 | 98 |
| D{2,6} | 60 | 0.005 | 12 | 0.249 | 615 |
| D{2,8} | 63 | 0.001 | 3 | 0.277 | 851 |
| D{3,6} | 64 | —$^a$ | —$^a$ | 0.162 | 502 |
| D{3,8} | 67 | 0.7 · 10$^{-3}$ | 3 | 0.029 | 127 |

$^a$Formation of a gel

For applications in fluorous bi-phasic catalysis and for catalyst recycling by fluorous phase extraction techniques an important feature of the fluorous aryl phosphines and the derived catalytic complexes is the partition coefficient P(P=C$_{fluorous\ phase}$/C$_{organic\ phase}$. C=concentration) in fluorous bi-phasic systems. To demonstrate the fluorphase affinity of phosphines bearing fluorous tail coupled to the spacer in fluorous bi-phasic systems, partition coefficients of the fluorous aryl phosphines D{m,x} were determined in several fluorous bi-phasic solvent combinations (Table 2 and FIG. 4). These data reflect a similar trend as was observed for their solubility data, i.e. there appears to be an optimum in fluorphase affinity for D{2,6} and D{2,8} except for the c-C$_6$F$_{11}$CF$_3$/n-pentane bi-phasic system, where a steady increase of P with the wt % of fluorine in D{m,x}, reaching a climax for D{3,8}, was found. A high fluoro phase affinity was found for D{2,8} in c-C$_6$F$_{11}$CF$_3$/n-octane (P=11).

TABLE 2

Fluorous Partition Coefficients of Fluorous Triaryl Monophosphines D{m,x} at 0° C. in 1:1 mixture (v/v) of c-C$_6$F$_{11}$CF$_3$ and Organic Solvent (P = c$_{fluorous\ phase}$/c$_{organic\ phase}$).$^a$

| compound | F content (wt %) | toluene/ c-C$_6$F$_{11}$CF$_3$ (T$_c$ = 89° C.)$^b$ | n-octane/ c-C$_6$F$_{11}$CF$_3$ (T$_c$ = 42° C.)$^b$ | n-pentane/ c-C$_6$F$_{11}$CF$_3$ (T$_c$ ~ 10° C.) |
|---|---|---|---|---|
| D{0} | 0 | 0.007 | — | — |
| D{1,6} | 50 | 0.13 | 0.42 | 0.53 |
| D{1,8} | 55 | 1.06 | 1.4 | 0.78 |
| D{2,6} | 60 | 3.8 | 6.6 | 2.0 |
| D{2,8} | 63 | 3.8 | 11 | 3.3 |
| D{3,6} | 64 | 2.1 | 3.7 | 5.3 |
| D{3,8} | 67 | 1.0 | 4.8 | 7.0 |

$^a$Derived from analysis of each of the two phases on phosphorus by ICP-AAS. The estimated experimental error is <±1 in the last digit.
$^b$Lo Nostro, P. Adv. in Colloid and Interface Sci. 1995, 56, 245–287.

As a demonstration of the fluorphase solubility of fluorous diphosphines with fluorotail containing spacer, diphosphines G{m,x} were tested for their solubility in perfluorinated solvents. The result are summarised in Table 3. For m>1 a clear preferential solubility in the fluorinated solvent was found.

TABLE 3

Solubility of dppe[a] and Fluorous and Non-Fluorous dppe Derivatives G{m,x} in Perfluorinated and Non-Fluorinated Solvents.

| Compound | solubility at room temperature[b] | | | melting range (° C.) |
|---|---|---|---|---|
| | THF | toluene | FC-72[c] | |
| dppe | + | − | − | 134–138 |
| G{0} | + | d | − | 186–189 |
| G{1,6} | + | + | − | 136–138 |
| G{1,8}} | − | − | − | 155–159 |
| G{2,6} | + | d | + | oil |
| G{3,6} | − | − | + | oil |

[a]dppe = bis(diphenylphosphino)ethane.
[b]+: >0.1 g/ml, −: <0.01 g/ml.
[c]FC-72: mixture of perfluorinated hexanes.
[d]Not determined.

Application of the Fluorous Monophosphines and Diphosphines in Catalysis

The fluorous monophosphine and diphosphine compounds according to the invention can serve as ligands for transition metal complexes that have potential as catalysts or catalyst precursors for fluorous phase homogeneous catalysis and fluorous bi-phasic catalysis.

The invention accordingly relates to metal complexes comprising at least one of these monophosphines or diphosphines as well as the preparation of these complexes and the use of these complexes and these phosphines as catalyst or catalyst precursors for fluorous phase and/or fluorous bi-phasic catalytic processes.

Preferred metal complexes are those containing iron, ruthenium, osmium, cobalt, rhodium, iridium, nickel, palladium and/or platinum, most preferably rhodium, iridium, nickel, palladium and/or platinum.

Preferred catalytic chemical processes are hydroformylation, hydrosilylation, hydroboration, carbonylation, Heck-type reactions, oligo- and polymerisations, cross-coupling reactions and hydrogenation of unsaturated compounds, preferably alkenes.

Representative examples of metal complexes of the fluorous phosphines and diphosphines developed are listed in Table 4. They have been prepared by modification of classical procedures (see examples for details).

TABLE 4

Fluorous Metal Phosphine and Diphosphine Complexes and their Characteristic $^{31}$P-NMR Spectroscopic Data.

| Complex no. | Formula | δ (multiplicity) | $^1J_{P,M}$ (Hz) | $^2J_{P,P}$ (Hz) |
|---|---|---|---|---|
| H{1,6}[a] | (D{1,6})$_3$RhCl | 48.0 (dt) | 190 | 37.8 |
| | | 31.4 (dd) | 143 | 37.6 |
| H{1,8}[a] | (D{1,8})$_3$RhCl | 48.0 (dt) | 192 | 37.8 |
| | | 31.4 (dd) | 145 | 37.4 |
| I{1,6}[b] | (G{1,6})Rh(COD)]BPh$_4$ | 56.1 (d) | 148 | — |
| J{2,6}[c] | (G{2,6})NiCl$_2$ | 58.1 (s) | — | — |
| K{1,6}[b] | (G{1,6})PtCl$_2$ | 41.9 (s) | 3604[e] | — |
| K{2,6}[d] | (G{2,6})PtCl$_2$ | 42.0 (s) | 3568[e] | — |

[a]In FC-72/C$_6$D$_6$, 1:1 (v/v).
[b]In CDCl$_3$.
[c]In C$_6$D$_6$/C$_6$F$_6$, 1:1 (v/v)
[d]In CDCl$_3$/CF$_3$C$_6$H$_5$, 1:1 (v/v).
[e]Satellites.

Furthermore the invention relates to the separation, selective extraction and/or recycling of fluorous metal complexes, catalysts and/or catalyst precursors containing at least one of the fluorous monophosphine and diphosphine ligands according to the invention and which is based on the preferential solubility of these complexes in perfluorinated or partially fluorinated solvents and/or their fluor phase affinity in multiphase solvent systems consisting of at least one per- or polyfluorinated solvent phase and a non-fluorinated hydrocarbon phase. A preferred embodiment of the invention concerns the selective extraction/separation of soluble metal catalysts from a reaction mixture comprising organic reagents and reaction products and the reuse of these catalysts. The successful application of the fluorous catalysts developed and their efficient recycling using fluorous bi-phasic separation techniques was demonstrated by a rhodium catalysed hydrogenation of 1-alkenes.

Figure 5:
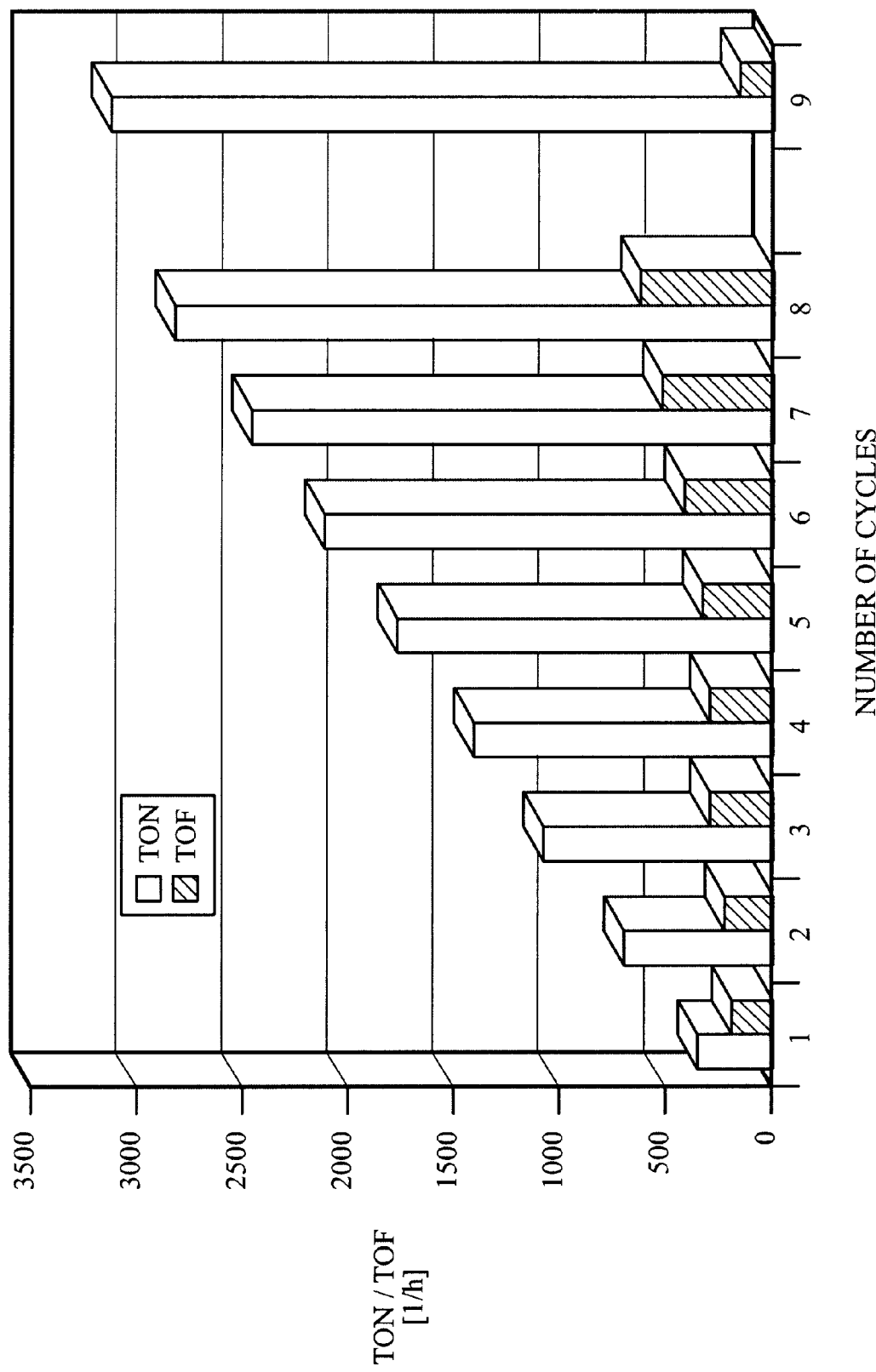
FIG. 5. Plot of turn over number (TON) and turn over frequency (TOF) for nine cycles. Conditions: catalyst=H{1, 8}; solvent=CF$_3$C$_6$F$_{11}$, T=80° C., p(H$_2$)=1 bar, [1-octene]/[Rh]=365, [Rh]$_0$=0.0087 mol/L. Fresh c- CF$_3$C$_6$F$_{11}$ added in 9$^{th}$ cycle as compensation for losses of fluorous solvent.

It was found that rhodium complexes H{1,6} and H{1,8} obtained from [(COD)RhCl]$_2$ (COD=cyclooctadiene) and fluorous phosphines D{1,6} and D{1,8}, respectively, are active catalysts for hydrogenation of 1-alkenes under single phase fluorous conditions at 80° C. (Table 5). In this respect compounds H{1,6} and H{1,8} are true fluorous equivalents of the classical Wilkinson's hydrogenation catalyst (PPh$_3$)$_3$RhCl. The hydrogenation products were readily isolated from the catalyst layer by cooling of the reaction mixture to 0° C. followed by phase separation of the resulting biphasic system. In this way hydrogenation of 1-octene afforded n-octane in >95% yield (GC, GC-MS). Less than 4.3% internal olefins resulting from isomerization were present. In case of H{1,8} it was possible to recycle the fluorous catalyst layer multiple times allowing high turnover numbers and high conversions per cycle (Table 5 and FIG. 5).

TABLE 5

Catalytic Hydrogenation[a] of 1-Octene using H{1,6} and H{1,8} as Pre-catalysts

| Complex | cycle | conv. [%] | t½ (min) | TOF$_{50\%}$ (h$^{-1}$) | TON (cumulative) | Leaching[b] Rh (%) | P (%) |
|---|---|---|---|---|---|---|---|
| H{1,6}[c] | 1 | 95 | 56 | 298 | 531 | 0.27 | 8.1 |
| H{1,8}[d] | 1 | 92 | 69 | 177 | 337 | 0.11 | 2.34 |
| | 2 | 96 | 58 | 212 | 688 | 0.05 | 2.06 |
| | 3 | 99 | 47 | 261 | 1048 | 0.10 | 3.24 |
| | 4 | 92 | 43 | 277 | 1383 | 0.11 | 3.20 |
| | 5 | 99.8 | 40 | 304 | 1747 | 0.18 | 3.52 |
| | 6 | 96.8 | 30 | 397 | 2100 | 0.08 | 2.15 |
| | 7 | 94 | 24 | 507 | 2444 | 0.05 | 2.34 |
| | 8 | 99.7 | 20 | 617 | 2808 | 0.33[e] | 4.70[e] |
| | 9[f] | 85 | 75 | 142 | 3117 | 0.08 | 3.41 |

[a]Conditions: solvent = c-CF$_3$C$_6$F$_{11}$, T = 80° C., p(H$_2$) = 1 bar.
[b]At T = 0° C., estimated error of ICP/AAS analysis ± 0.013%.
[c]Containing 10 mol % of D{1,6}, [1-octene]/[Rh] = 559, [Rh]$_0$ = 0.0060M.
[d][1-octene]/[Rh] = 365, [Rh] = 0.0087M in the initial cycle.
[e]High value due to experimental error during phase separation.
[f]Fresh c-CF$_3$C$_6$F$_{11}$ added as compensation for losses of fluorous solvent.

It was found for H{1,8} that the activity increased with the number of cycles (up to TOF~600 h$^{-1}$ in the 8$^{th}$ cycle). Without being bound by theory, this is most probably caused by the combined effects of a non-zero order rate dependence in rhodium and olefins, (observed) losses of fluorous solvent due to evaporation during phase separation under H$_2$-flow and non-zero miscibility of c-C$_6$F$_{11}$CF$_3$ in the product layer even at 0° C. (ca 5% by volume). Consequently, an average loss of flourous solvent of ca 12% per cycle (ca 0.25 mL) took place. However, restoring the amount of c-C$_6$F$_{11}$CF$_3$ in the 9$^{th}$ cycle to its initial volume showed that the catalyst activity had dropped by 19% (entry 9, Table 6).

Rhodium leaching into the organic phase (as determined by ICP-AAS) was low. On average 0.12% of Rh per cycle was lost corresponding to a rhodium concentration of 3 ppm (by weight) in the product phase. Over 9 cycles only 1% of rhodium was lost despite of the phase separation method used. Leaching was higher for less fluorous pre-catalyst H{1,6}: 0.3% (6 ppm) of rhodium was present in the organic phase after phase separation.

The amount of leached rhodium allows to calculate the average partition coefficients (P) of the rhodium species present during phase separation (Table 6). The values found, clearly demonstrate a significant positive effect of longer fluorochains and lower temperature on the value of P. The partitioning of rhodium found for H{1,8} at 0° C. is higher than reported for RhCl [P(CH$_2$)$_2$(CF$_2$)$_n$CF$_3$)$_3$]$_3$ (696 and 811 for n=5 and 7, respectively, in c-C$_6$F$_{11}$CF$_3$/toluene at 27° C., Juliette, J. J. J.; Rutherford, D.; Horváth, I. T.; Gladysz, J. A.; *J. Am. Chem. Soc.* 1999, 121, 2696–2704.). Although a direct comparison is difficult because of the different solvent system used, this result is considered good for arylphosphine rhodium complexes taking into account the significant lower partition coefficients of the fluorous arylphosphines (D{1, 6}: P=0.13; D{1,8}: P=1.06, in c-C$_6$F$_{11}$CF$_3$/toluene at 0° C.) as compared to the fluorous alkylphosphines P [(CH$_2$)$_2$(CF$_2$)$_n$CF$_3$)$_3$]$_3$ (n=5: P=82; n=7: P=332 in c-C$_6$F$_{11}$CF$_3$/toluene at 27° C., Juliette, J. J. J.; Horváth, I. T.; Gladysz, J. A.; *Angew. Chem. Int. Ed. Engl.* 1997, 36, 1610–1612).

TABLE 6

Average Partitioning Coefficients (P)[a] of Rhodium Species present in the Fluorous Biphasic Product Mixture Resulting from Hydrogenation of 1-Octene

| pre-catalyst | F content of D{1,x} (wt %) | P T = 25° C. | P T = 0° C. |
|---|---|---|---|
| H{1,6} | 48.7 | 76[b] | 293[b] |
| H{1,8} | 53.2 | n.d. | 1052[c] |

[a]Calculated from of the amount of Rh found in the organic product phase by ICP-AAS analysis.
[b]Obtained from data of 1 cycle.
[c]Average value over nine cycles.

The retention of free uncoordinated fluorous phosphine can be used for recycling the intact catalyst system. In fact, small amounts of fluorous phosphine were present in the alkane product phases (H{1,6}: 130 ppm, 8% of total phosphorus in precatalyst; H{1,8}: 64 ppm, 3% of total phosphorus in precatalyst) indicating that leaching of fluorous ligand is more significant than that of rhodium and to a large extent responsible for the lower recycling efficiency of the H{1,6}-derived catalyst solution.

To be able to directly compare the activities of fluorous derivatives H{1,6} and H{1,8} with non-fluorous [P(C$_6$H$_4$-4-SiMe$_3$)$_3$]$_3$RhCl (H{0}) and the conventional Wilkinson catalyst (PPh$_3$)$_3$RhCl, homogeneous hydrogenation of 1-octene were carried out under single phase conditions in the hybrid solvent α,α,α-trifluorotoluene at atmospheric H$_2$ pressures. The results obtained with the different pre-catalysts are listed in Table 7. Highest rates of hydrogen uptake (14.2 mol.L$^{-1}$.h$^{-1}$) were measured for 1c at relatively high rhodium and olefine concentrations (entry 2, Table 7). Under these conditions a zero-order dependence in [1-octene] was found up to ca 80% conversion resulting in a linear conversion versus time plot. In all other experiments ([Rh]=4.0–8.0 mM, [1-octene]$_0$=1.46 M) rates of hydrogen uptake were lower (<11 mol.L$^{-1}$.h$^{-1}$) and conversion versus time plots corresponded to a rate law -d[1-octene]/dt=k$_{obs}$.[1-octene] for >98% conversion allowing to evaluate catalyst activity in terms of the observed first order rate constant k$_{obs}$. Since for these experiments the rates of dihydrogen uptake were well below the maximum value obtained in entry 2, diffusion limitation of H$_2$ can be excluded. In addition to k$_{obs}$, turn over frequencies (TOF in mol.mol$^{-1}$.h$^{-1}$) were derived from the tangent of a 4$^{th}$order polynomal fit to conversion versus time plots at 25% conversion and serve as a measure of catalyst activity independent of any assumed kinetic relationship with substrate.

TABLE 7

Comparison of Fluorous and Non-Fluorous Pre-catalysts RhCl[P(C$_6$H$_4$-p-R)$_3$]$_3$ in the Hydrogenation of 1-Octene[a]

| Entry | Catalyst precursor | [Rh] (mM) | [1-octene] (M) | conversion (%) | TON[b] | k$_{obs}$[c] (h$^{-1}$) | TOF$_{(25\%)}$[d] (h$^{-1}$) |
|---|---|---|---|---|---|---|---|
| 1 | H{0} | 4.0 | 1.46 | 92 | 336 | 7.5(2) | 1610 |
| 2 | H{0} | 8.0 | 2.92 | 99 | 361 | —[e] | 1910 |
| 3 | H{1,6}[c] | 4.0 | 1.46 | 99 | 363 | 4.2(1) | 1110 |
| 4 | (PPh$_3$)$_3$RhCl | 4.0 | 1.46 | 98 | 358 | 4.0(1) | 960 |
| 5 | H{1,8}[d] | 4.0 | 1.46 | 99 | 355 | 3.2(1) | 870 |

[a]Conditions: T = 80° C., p(H$_2$) = 1 bar, solvent: α,α,α-trifluorotoluene, stirring speed = 900 rpm.
[b]TON = turn over number (mole of olefin/mole of Rh).
[c]Obtained by fitting the data to X$_t$ = [1-exp(-k$_{obs}$·t)] (X$_t$ = conversion).
[d]TOF = turn over frequency (mole of olefin/mole of Rh/hour) at 25% conversion.
[e]Zero order in olefin up to 80% conversion, k$_{obs}$ = 14.2(1) mol.L$^{-1}$.h$^{-1}$.

From Table 7 it can be derived that [P($C_6H_4$-4-Si$Me_3$)$_3$]$_3$RhCl (H{0}) displays a high activity being >1.5 times more active than Wilkinson's catalyst. This result shows the beneficial influence of the para-silyl substitution on catalytic activity. The H{1,6} (entry 3) is comparable in activity to RhCl (PPh$_3$) (entry 4) despite its fluorotail functionalisation and the presence of small quantities of free phosphine (<10%) which are known to partially inhibit catalytic activity (Montelatici, A.; van der Ent, A.; Osborn, J. A.; Wilkinson, G.; *J. Chem. Soc.*, (A), 1968, 1054–1058 and Jardine, F. H. in *Progress Inorg. Chem.*, Lippard, S. J. (ed), John-Wiley & Sons, New York, 1981, Vol. 28, p. 117–131.) The somewhat lower activity of H{1,8} (entry 5) suggests a small negative electronic influence on catalytic activity caused by the longer fluor tail but solvation effects cannot be excluded, however. The overall activities of H{1,6} and H{1,8} in perfluormethylcyclohexane and solvent α,α,α-trifluorotoluene also compare favourably with turn over frequencies for 1-alkene hydrogenation by Wilkinson's catalyst in conventional solvents (TOF=150–600 h$^{-1}$ for hydrogenation of 1-heptene in benzene, Osborne, J. A.; Jardine, F. H.; Young, J. F.; Wilkinson, G.; *J. Chem., Soc.*, (A), 1966, 1711–1732).

Figure 6:
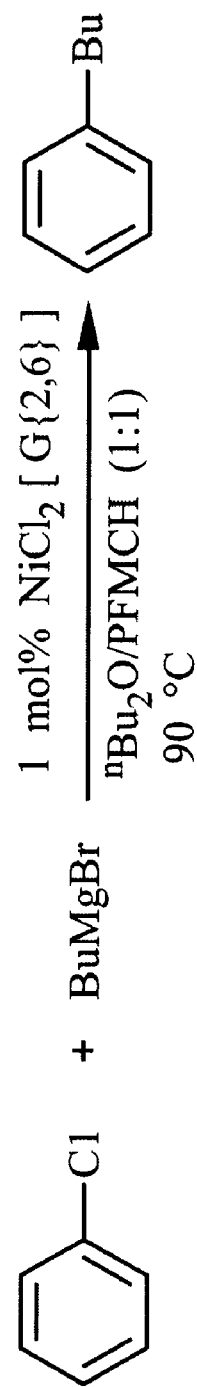
FIG. 6. Nickel-catalyzed cross-coupling reaction of butyl-magnesium bromide and chlorobenzene in a fluorous biphasic reaction medium using a fluorous phase soluble diphosphine nickel dichloride complex as catalyst precursor.

Another example concerns a nickel-catalysed cross-coupling reaction of butylmagnesium bromide and chlorobenzene in a fluorous bi-phasic reaction medium using a fluorous phase soluble diphosphine nickel dichloride complex as catalyst precursor (FIG. 6). This example demonstrates the compatibility of the catalysts with the fluorous bi-phasic reaction medium employed and that at least partial catalyst recovery is possible using the technique of fluor-phase immobilisation (Table 8). It should be noted that no attempts were made to optimise the recycling efficiency.

EXAMPLES

General Remarks

Reactions were conducted under dinitrogen atmosphere unless noted otherwise. Solvents were employed as follows: benzene, toluene, n-pentane, n-hexane, diethyl ether distilled from Na/benzophenone; FC-72, c-$C_6F_{11}CF_3$, $CF_3C_6H_5$ (Acros, Alfa) degassed and stored over molecular sieves; $C_6F_6$ (Acros), $C_6D_6$, CDCl$_3$, n-$C_6D_{14}$ (Cambridge Isotope Laboratories, Aldrich) degassed and stored over molecular sieves Reagents were utilised as follows: $C_xF_{2x+1}$CH=CH$_2$ (x=6, 8) (Acros), $C_xF_{2x+1}$CH$_2$CH$_2$I (x=6, 8) (Lancaster), Mg turnings (Norsk Hydro, 99.8+%) used as received; HSiCl$_3$, HSi(Me)Cl$_2$, HSiMe$_2$Cl, H$_2$PtCl$_6$ (aq) (Acros) stored under nitrogen and used as received. Chlorobenzene and di-n-butyl ether were distilled and stored over molecular sieves under dinitrogen atmosphere before use. Elemental and ICP-AAS analyses were carried out by H. Kolbe, Mikroanalytisches Laboratorium, Mühlheim an der Ruhr. NMR spectra were obtained on Varian INOVA 300 and Varian MERCURY 200 spectrometers. $^1$H-, $^{13}$C-, $^{29}$Si-NMR spectra were referenced relative to TMS, $^{31}$P-NMR relative to 85% H$_3$PO$_4$ and $^{19}$F-NMR relative to CFCl$_3$ (external). The $^{19}$F-decoupler frequency in $^{13}$C{$^{19}$F}NMR experiments was either set to [a] δ=-121 or [b] δ=-81 to $^{19}$F-decouple either the CF$_2$— or the CF$_3$-groups respectively.

1. $C_xF_{2x+1}$ (CH$_2$)$_2$SiMe$_2$Cl (C{1,x}, x=6, 8) by Hydrosilylation

See also Améduri, B.; Boutevin, B.; Nouiri, M.; Talbi, M.; *J. Fluorine Chem.* 1995, 74, 191.

C{1,6}

17.3 g (50.0 mmol) of $C_6F_{13}$CH=CH$_2$ and 20.0 mL (180 mmol) of HSiMe$_2$Cl were combined, H$_2$PtCl$_6$ (aq) (40 mg) was added and the mixture was refluxed for 2 hours. Another 20 mg of catalyst were added followed by refluxing over night and fractional distillation. Yield: 13.2 g (29.9 mmol, 60%) of C{1,6}; b.p. 79° C. (0.1 torr). $^1$H NMR (CDCl$_3$) δ2.14 (m, 2 H), 1.04 (m, 2H), 0.46 (s, 6H , $^2J_{Si,H}$=7.0 Hz). $^{19}$F NMR (δ, $C_6D_6$) -81.4 (tt, 3 F, $J_{F,F}$=9.8 Hz, $J_{F,F}$=2.4 Hz), -114.3 (m, 2 F), -122.6 (m, 2 F), -123.5 (m, 2 F), -123.8 (m, 2 F), -126.9 (m, 2 F). $^{13}$C{$^1$H} NMR (δ, CDCl$_3$) 25.2 (t, $^2J_{C,F}$=24.5 Hz), 8.63 (t, $^3J_{C,F}$=2.9 Hz), 1.25 (s, $^1J_{C,Si}$=57.7 Hz).

C{1,8}

Following a similar procedure as for C{1,6}, 22.3 g (50.0 mmol) of $C_8F_{17}$CH=CH$_2$ and 21.7 mL (0.2 mol) of HSiMe$_2$Cl yielded 21.4 g (39.6 mmol, 79.2%) of C{1,8}; b.p.: 87° C. (0.1 torr). $^1$H NMR ($C_6D_6/C_6F_6$, 1:1 (v/v)) δ2.16 (m, 2H), 0.95 (m, 2H), 0.32 (s, 6H). $^{19}$F NMR ($C_6D_6/C_6F_6$, 1:1 (v/v)) δ-81.2 (m, 3 F), -115.8 (m, 2 F,), -121.5 (m, 6 F), -122.4 (m, 2 F), -122.9 (m, 2 F), -126.0 (m, 2 F). $^{29}$Si NMR ($C_6D_6/C_6F_6$ 1:1 (v/v)) δ30.8 (s). $^{13}$C{$^{19}$F}$^b$ NMR (CDCl$_3$) δ118.5 (m), 117.5 (t, $^2J_{C,F}$=27.5 Hz), 111.3 (tm, $^1J_{C,F}$=268 Hz), 108.8 (tt, $^1J_{C,F}$=272 Hz, $^2J_{C,F}$=28.7 Hz), 25.6 (tm, $^1J_{C,H}$=131 Hz), 8.93 (t, $^1J_{C,H}$=121 Hz), 1.46 (q, $^1J_{C,H}$=121 Hz).

2. Grignard of $C_xF_{2x+1}$CH$_2$CH$_2$I (x=6, 8)

60 g (2.5 mol) of Mg turnings were placed in a three necked round bottom flask equipped with a magnetic stirring bar. While evacuating and heating the flask with a Bunsen burner the Mg turnings were stirred until a Mg-mirror had formed. After reaching room temperature the flask was filled with ca. 250 mL of diethyl ether and 25 g of $C_xF_{2x+1}$ (CH$_2$)$_2$I (52.7 mmol, x=6; 43.5 mmol, x=8) of 1H,1H,2H,2H-perfluoroalkyl iodide dissolved in 60 mL diethyl ether were slowly added (ca. 1 drop per 15 s) under vigorous stirring. The reaction mixture was stirred for another 15 h at room temperature affording a slightly yellow solution of the Grignard. All Grignard solutions used were freshly prepared and filtrated (G4 glass filter). Judging from a number of reactions with the hydrochlorosilanes to produce compounds B{m,x} the yields of the Grignard reaction were estimated to be ≧79% (x=6) and ≧75% (x=8).

3. HSiMe$_{3-m}$[(CH$_2$)$_2$$C_xF_{2x+1}$]$_m$ (B{m,x}, m=1, 2, 3; x=6, 8)

For compounds B{3,x} also see Boutevin, B.; Guida-Pietrasanta, F.; Ratsimihety, A.; Caporiccio, G.; Gornowitz, G.; *J. Fluorine Chem.*, 1993, 60, 211; Améduri, B.; Boutevin, B.; Nouiri, M.; Talbi, M.; *J. Fluorine Chem.* 1995, 74, 191; Studer, A.; Jeger, P.; Wipf, P.; Curran, D. P.; *J. Org. Chem.*, 1997, 62, 2917.

General Procedure

The $C_xF_{2x+1}$(CH$_2$)$_2$I-Grignard solutions were treated with a stoichiometric amount of the respective chlorosilane (assuming 90% conversion of the Grignard reaction) and stirred over night. The reaction mixtures, which either consisted of a liquid biphasic system or a white suspension, were quenched with water (100 mL). After phase separation the organic phases were combined with two 20mL diethyl ether extracts of the water phase and dried over MgSO$_4$. Volatiles were removed in vacuo. The light-yellow oils (B{2,6}, B{3,6}, B{1,8}) and white waxy solids (B{2,8}, B{3,8}) contained ≦10% of Wurtz coupling product, which was removed by Kugelrohr distillation or by fractional distillation (B{1,6}).

B{1,6}

A Grignard solution prepared from 12.5 g (26 mmol) $C_6F_{13}$(CH$_2$)$_2$I, treated with 3.3 mL (2.8 g, 30 mmol) of HSiMe$_2$Cl, yielded 7.32 g (18.0 mmol, 68% based on 1H,1H,2H,2H-perfluoroalkyl iodide); b.p.: 60–62° C. (0.1 torr). $^1$H NMR (CDCl$_3$): δ3.91 (non, $^1J_{Si,H}$=180 Hz, $^3J_{H,H}$=3.4 Hz, 1H), 2.08 (m, 2H), 0.83 (m, 2H), 0.12 (d, $^3J_{H,H}$=3.4

Hz, $^2J_{Si,H}$=7.0 Hz, 6H). $^{19}$F NMR (δ, CDCl$_3$) −81.4 (t, $J_{F,F}$=9 Hz, 3 F), −115.5 (quin, $J_{F,F}$=9 Hz, 2 F), −121.4 (m, 2 F), −122.3 (m, 2 F), −122.8 (m, 2 F), −125.7 (m, 2 F); $^{29}$Si{$^1$H} NMR (CDCl$_3$); δ−11.1. $^{13}$C{$^1$H} NMR (CDCl$_3$); δ118.5 (tt, $^1J_{C,F}$=253 Hz, $^2J_{C,F}$=30.4 Hz), 117.4 (qt, $^1J_{C,F}$= 287 Hz, $^2J_{C,F}$=32.3 Hz), 26.6 (t, $^2J_{C,F}$=24 Hz), 3.88, −4.73 ($^1J_{Si,C}$=51 Hz). $^{13}$C{$^{19}$F}$^a$ NMR (CDCl$_3$); 118.5 (m), 117.5 (q, $^1J_{C,F}$=154 Hz), 111.5, 111.3, 110.5, 108.7 (q, $^2J_{C,F}$=20 Hz), 26.6 (ttd, $^1J_{C,H}$=130 Hz, $^2J_{C,H}$=5.5 Hz, $^3J_{C,H}$2.5 Hz), 3.88 (tm, TC,H=127 Hz), −4.73 (qdt, $^1J_{C,H}$=122 Hz, $^2J_{C,H}$= 7.6 Hz, $^3J_{C,H}$=2.0 Hz).

B{2,6}

A Grignard solution prepared from 12.5 g (26 mmol) of C$_6$F$_{13}$(CH$_2$)$_2$I, treated with 1.24 mL (1.38 g, 12.0 mmol) of HSiMeCl$_2$ yielded 7.68 g (10.4 mmol, 79% based on 1H,1H, 2H,2H-perfluoroalkyl iodide), b.p.: 96° C. (0.1 torr). $^1$H NMR (CDCl$_3$); δ3.91 (oct, $^1J_{si,H}$=187 Hz, $^3J_{H,H}$=3.8 Hz, 1H), 2.10 (m, 4H), 0.90 (m, 4H), 0.19 (d, $^3J$=3.8 Hz, 3 H). $^{19}$F NMR (δ, CDCl$_3$)−82.0 (m, 3 F), −117.1 (m, $J_{F,F}$=15 Hz, 2 F), −123.0 (m, 2 F), −124.0 (m, 2 F), −124.5 (m, 2 F), −127.3 (m, 2 F). $^{29}$Si{$^1$H} NMR (CDCl$_3$): δ−6.78 (s). $^{13}$C{$^1$H} NMR (CDCl$_3$): δ26.4 (t, $^2J_{C,F}$=23 Hz), 2.33 (s), −6.74 (s)

B{3,6}

A Grignard solution prepared from 31.52 g (66.5 mmol) C$_6$F$_{13}$(CH$_2$)$_2$, treated with 2.04 mL (2.7 g, 19.9 mmol) of HSiCl$_3$ yielded 18.4 g (17.2 mmol, 77.6% based on 1H,1H, 2H,2H-perfluoroalkyl iodide); b.p.: 150° C. (0.1 torr). $^1$H NMR (CDCl$_3$): δ3.94 (m, $^1J_{si,H}$=186 Hz, 1H), 2.12 (m, 6 H), 0.97 (m, 6 H). $^{19}$F NMR (CDCl$_3$): δ−81.5 (t, $J_{F,F}$=12 Hz, 3 F), −116.5 (m, $J_{F,F}$=15 Hz, 2 F), −122.5 (m, 2 F), −123.5 (m, 2 F), −124.0 (m, 2 F), −126.8 (m, 2 F). $^{29}$Si{$^1$H} NMR (CDCl$_3$): δ−2.65 (s). $^{13}$C{$^1$H} NMR (δ, CDCl$_3$) 118.1 (tt, $^1J_{C,F}$=255 Hz, $^2J_{C,F}$=31.4 Hz), 117.5 (qt, $^1J_{C,F}$=288 Hz, $^2J_{C,F}$=33.0 Hz), 26.3 (t, $^2J_{C,F}$=23.8 Hz), 0.83. $^{13}$C{$^{19}$F}$^a$ NMR (CDCl$_3$): δ118.1 (m), 117.4 (q, $^1J_{C,F}$=232 Hz), 111.3, 111.2, 110.4, 108.7 (q, $^2J_{C,F}$=25.7 Hz), 26.3 (ttd, $^1J_{C,H}$=130 Hz, $^2J_{C,H}$=5.4 Hz, $^3J_{C,H}$=2.4 Hz), 0.84 (tm, $^1J_{C,H}$=123 Hz).

B{2,8}

A Grignard solution prepared from 26.2 g (45.6 mmol) C$_8$F$_{17}$(CH$_2$)$_2$I, treated with 2.13 mL (2.36 g, 20.5 mmol) HSiMeCl$_2$ yielded 14.9 g (15.9 mmol, 69.7% based on 1H,1H,2H,2H-perfluoroalkyl iodide); m.p.: 38–40° C. Anal. Calcd for C$_{21}$H$_{12}$F$_{34}$Si: C 26.85, H1.28, F 68.84, Si 2.98. Found: C 26.95, H1.36, F 68.66, Si 2.91. $^1$H NMR (6, CDCl$_3$) 3.91 (oct, $^1J_{Si,H}$=191 Hz, $^3J_{H,H}$=3.6 Hz, 1H), 2.11 (m, 4H), 0.91 (m, 4 H), 0.20 (d, $^3J_{H,H}$=3.6 Hz, 3H). $^{19}$F NMR (δ, CDCl$_3$) −81.7 (m, 3 F), −116.9 (m, $J_{F,F}$=12 Hz, 2 F), −122.7 (m, 6 F), −123.5 (m, 2 F), −124.1 (m, 2 F), −127.0 (m, 2 F). $^{29}$Si NMR (δ, CDCl$_3$) −6.81 (d, $^1J_{SiH}$=192 Hz). $^{29}$Si{$^1$H} NMR(δ, CDCl$_3$) −6.77. $^{13}$C{$^1$H} NMR (δ, CDCl$_3$) 26.4 (t, $^2J_{C,F}$=24 Hz), 2.26, −6.86. $^{13}$C{$^{19}$F}$^a$ NMR (δ, CDCl$_3$) 118.4 (m), 117.5 (q, $^1J_{C,F}$=269 Hz), 111.7 , 111.5, 111.2, 111.1, 110.6, 108.8 (q, $^2J_{C,F}$=26.3 Hz), 26.6 (tm, $^1J_{C,H}$=130 Hz), 2.42 (tm, $^1J_{C,H}$=119 Hz), −7.01 (qm, $^1J_{C,H}$= 121 Hz).

B{3,8}

A Grignard solution prepared from 24.5 g (42.6 mmol) C$_8$F$_{17}$(CH$_2$)$_2$I, treated with 1.08 mL (1.44 g, 10.7 mnmol) HSiCl$_3$ yielded 14.7 g (10.7 mmol, 75.3% based on 1H,1H, 2H,2H-perfluoroalkyl iodide); m.p.: 91° C. Anal. Calcd for C$_{30}$H$_{13}$F$_{51}$Si: C 26.27, H 0.95, F 70.71, Si 2.04. Found C 26.16, H 1.10, F 70.62, Si 2.18. $^1$H NMR (CDCl$_3$/C$_6$F$_6$ 3:1 (v/v)): δ3.9 (m, $^1J_{Si,H}$=192 Hz, 1H), 2.13 (m, 6 H), 1.05 (m, 6 H). $^{19}$F NMR (CDCl$_3$/C$_6$F$_6$ 3:1 (v/v)) δ−81.7 (m, 3 F), −116.9 (m, 2 F), −122.7 (m, 6 F), −123.6 (m, 2 F), −124.2 (m, 2 F), −127.0 (m, 2 F). $^{29}$Si{$^1$H} NMR (CDCl$_3$/C$_6$F$_6$ 3:1 (v/v)): δ−2.38. $^{13}$C{$^{19}$F}$^a$ NMR (δ, CDCl$_3$/C$_6$F$_6$ 3:1 (v/v)): δ118.5 (m), 117.8 (q, $^1J_{C,F}$=262 Hz), 111.8 (s), 111.8 (s), 111.4 (s), 111.4 (s), 110.9 (s), 109.0 (q, $^2J_{C,F}$=24.4 Hz), 26.6 (tm, $^1J_{C,H}$=130 Hz), 1.0 (tm, $^1J_{C,H}$=124 Hz).

4. [C$_x$F$_{2x+1}$(CH$_2$)$_2$]$_m$SiMe$_{3-m}$Br (C{m,x}, m=2, 3; x=6, 8)

For compounds C{3,x} also see Studer, A.; Curran, D. P.; Tetrahedron, 1997, 53, 6681; Studer, A.; Jeger, P.; Wipf, P.; Curran, D. P.; *J. Org. Chem.*, 1997, 62, 2917.

General Procedure

The silanes B{m,x} were either dissolved in n-hexane or n-hexane/FC-72 mixtures and a 2 fold excess of Br$_2$ was added to the reaction mixture at 0° C. After being stirred for 15 h at room temperature all volatiles were removed in vacuo. The slightly yellow or colorless oily or waxy residues or waxy solids, when necessary, were further purified by Kugelrohr, fractional distillation or recrystallisation.

C{2,6}

A solution of 25.4 g (34.3 mmol) of B{2,6} in 100 mL of n-hexane was treated with 3.51 mL (11.0 g, 68.7 mmol) of Br$_2$, yielding 27.6 g (34.0 mmol, 99.1% based on B{2,6}); b.p.: 105° C. (0.1 torr). $^1$H NMR (C$_6$D$_6$); δ1.93 (m, 4 H), 0.71 (m, 4H), 0.02 (s, 3H). $^{19}$F NMR (δ, C$_6$D$_6$) −81.5 (t, $J_{F,F}$=9 Hz, 3 F), −115.7 (m, $J_{F,F}$=15 Hz, 2 F), −122.3 (m, 2 F), −123.3 (m, 2 F), −123.5 (m, 2 F), −126.6 (m, 2 F). $^{29}$Si{$^1$H} NMR (δ, C$_6$D$_6$) 29.2. $^{13}$C{$^1$H} NMR (C$_6$D$_6$): δ118.8 (tt, $^1J_{C,F}$=255 Hz, $^2J_{C,F}$=30.6 Hz), 118.1 (qt, $^1J_{C,F}$= 289 Hz, $^2J_{C,F}$=33.0 Hz), 112.3 (tquin, $^1J_{C,F}$=268 Hz, $^2J_{C,F}$=32.0 Hz), 112.1 (tquin, $^1J_{C,F}$=271.3 Hz, $^2J_{C,F}$=31.8 Hz), 111.3 (tquin, $^2J_{C,F}$=272 Hz, $^2J_{C,F}$=31.7 Hz), 109.4 (tqt, $^1J_{C,F}$=260 Hz, $^2J_{C,F}$=30.5 Hz), 26.0 (t, $^2J_{C,F}$=23.8 Hz), 7.73, −0.38.

C{3,6}

A suspension of 11.8 9 (11.0 mmol) of B{3,6} in 100 mL of n-hexane was treated with 1.13 mL (3.54 g, 22.2 mmol) of Br$_2$, yielding 10.1 g (8.79 mmol, 79.9% based on B{3,6}) after fractional distillation; b.p.: 180° C. (0.1 torr). $^1$H NMR (C$_6$D$_6$/C$_6$F$_6$ 1:1 (v/v)): δ2.10 (m, 6H), 0.98 (m, 6H). $^{29}$Si{$^1$H} NMR (C$_6$D$_6$/C$_6$F$_6$ 1:1 (v/v)): δ30.0 (s). $^{13}$C{$^1$H} NMR (C$_6$D$_6$): δ119–109 (m), 26.2 (t, $^2J_{C,F}$=24.2 Hz), 6.42.

C{2,8}

A solution of 24.6 g (26.2 mmol) of B{2,8} in 400 mL of n-hexane was treated with 2.7 mL (8.4 g, 52.4 mmol) of Br$_2$, yielding 21.3 g (20.9 mmol, 79.8% based on B{2,8}) after recrystallization in benzene. m.p.: 55° C. Anal. calcd for C$_{21}$H$_{11}$BrF$_{34}$Si: C 24.77, H 1.08, Br 7.85, F 63.50, Si 2.75. Found C 24.87, H 1.15, Br 7.67, F 63.62, Si 2.69. $^1$H NMR (C$_6$D$_6$); δ2.00 (m, 4H), 0.84 (m, 4H), 0.12 (s, $^2J_{SiH}$=6.6 Hz, 3H). $^{19}$F NMR (δ, C$_6$D$_6$) −81.0 (m, 3 F), −115.2 (m, 2 F), −121.7 (m, 6 F), −122.5 (m, 2 F), −122.9 (m, 2 F), −126.0 (m, 2 F). $^{29}$Si{$^1$H} NMR (C$_6$D$_6$): δ29.1 (s). $^{13}$C{$^{19}$F}$^a$ NMR (C$_6$D$_6$): δ118.7 (m), 117.9 (q, $^1J_{C,F}$=272 Hz), 112.0, 111.7, 111.6, 111.1, 109.8 (m), 25.9 (tt, $^1J_{C,H}$=131 Hz, $^2J_{C,H}$=5.5 Hz), 7.61 (tm, $^1J_{C,H}$=122 Hz), −0.31 (qm, $^1J_{C,H}$=123 Hz).

C{3,8}

A biphase liquid system of 12.6 g (8.72 mmol) of B{3,8} in 40 mL of FC-72 and 30 mL of n-hexane was treated with 1.0 mL (3.12 g, 19.5 mmol) of Br$_2$, yielding 11.6 g (8.00 mmol, 91.7% based on B{3,8}) of pure C{3,8}; m.p.: 93° C. $^1$H NMR (C$_6$D$_6$/C$_6$F$_6$ 3:1 (v/v)): δ2.21 (m, 6H), 1.13 (m, 6 H). $^{19}$F NMR (C$_6$D$_6$/C$_6$F$_6$ 3:1 (v/v)): δ−81.6 (m, 3 F), −116.0 (m, 2 F), −121.9 (m, 6 F), −122.8 (m), −123.1 (m, 2 F), −126.3 (m, 2 F). $^{29}$Si{$^1$H} NMR (C$_6$D$_6$/C$_6$F$_6$ 3:1 (v/v)): δ30.1 (s).

5. p-[{C$_x$F$_{2x+1}$(CH$_2$)$_2$}$_m$SiMe$_{3-m}$]C$_6$H$_4$Br (E{m,x}, m=0, 1; x=6, 8)

General Procedure p-LiC$_6$H$_4$Br was obtained from p-iodobromobenzene and one equivalent of n-BuLi (1.5 M n-hexane solution), in n-pentane at 0° C. After 1 hour the suspension was centrifuged and the liquid was decanted from the white precipitate. The respective chlorosilane dissolved in 10 mL of THF was added at −78° C. to a suspension of p-LiC$_6$H$_4$Br in n-pentane. The reaction mixture was allowed to warm to room temperature and was stirred over night. After quenching with saturated NH$_4$Cl (aq), the water phase was extracted with two 20 mL portions of n-pentane. The combined organic phases were dried over MgSO$_4$. Fractional distillation afforded the pure products. Compounds 1,4-(RMe$_2$Si)$_2$C$_6$H$_4$ (R=Me, —(CH$_2$)$_2$C$_6$F$_{13}$, —(CH$_2$)$_2$C$_8$F$_{17}$) were obtained as side products.

E{0}

1.74 g (16.0 mmol) of Me$_3$SiCl, 5.0 9 (17.7 mmol) of p-iodobromobenzene and 11.8 mL (17.7 mmol) of n-BuLi in 80 mL n-pentane yielded 3.59 g (15.7 mmol, 98.1%) based on Me$_3$SiCl); b.p.: 238° C. $^1$H NMR (C$_6$D$_6$): δ7.34 (m, 2H), 7.05 (m, 2 H), 0.09 (s, 9 H). $^{13}$C{$^1$H} NMR (δ, C$_6$D$_6$) 139.4, 135.6, 131.6, 124.4, −0.82 (s). $^{29}$Si{$^1$H} NMR (C$_6$D$_6$/C$_6$F$_6$ 1:1 (v/v)): δ−3.67 (s).

E{1,6}

3.58 g (7.57 mmol) of C{1,6}, 2.4 g (8.48 mmol) p-Iodobromobenzene and 5.6 mL (8.4 mmol) of n-BuLi in 40 mL n-pentane yielded 3.53 g (6.29 mmol, 83.1% based on C{1,6}); b.p.: 104° C. (0.1 torr). $^1$H NMR (C$_6$D$_6$/C$_6$F$_6$ 1:1 (v/v)): δ7.25 (m, 2 H), 7.12 (m, 2 H), 2.02 (m, 2 H), 0.94 (m, 2 H), 0.22 (s, 6 H). $^{19}$F NMR (C$_6$D$_6$): δ−81.4 (m, 3 F), −116.4 (m, 2 F), −122.5 (m, 2 F), −123.5 (m, 2 F), −123.8 (m, 2 F), −126.7 (m, 2 F). $^{29}$Si{$^1$H} NMR (C$_6$D$_6$/C$_6$F$_6$ 1:1 (v/v)): δ−1.51. $^{13}$C{$^1$H} NMR (C$_6$D$_6$): δ136.3 (s), 135.6 (s), 131.9 (s), 125.0 (s), 119.3 (tt, $^1$J$_{C,F}$=255 Hz, $^2$J$_{C,F}$=29.8 Hz), 118.2 (qt, $^1$J$_{C,F}$=287 Hz, $^2$J$_{C,F}$=31.7 Hz), 112.3 (tquin, $^1$J$_{C,F}$=268 Hz), 112.2 (tquin, $^1$J$_{C,F}$=270 Hz, $^2$J$_{C,F}$=32.5 Hz), 111.3 (tquin, $^1$J$_{C,F}$=274 Hz, $^2$J$_{C,F}$=31.6 Hz), 109.5 (tqt, $^1$J$_{C,F}$=270 Hz, $^2$J$_{C,F}$=31.6 Hz), 26.5 (t, $^2$J$_{C,F}$=23.7 Hz), 5.56 (s, $^1$J$_{C,Si}$=50.5 Hz), −3.65 (s, $^1$J$_{C,Si}$=52.8 Hz).

E{1,8}

21.9 g (40.5 mmol) of C{1,8}, 12.6 g (44.5 mmol) of p-iodobromobenzene and 27 mL (40.5 mmol) of n-BuLi in 80 mL of n-pentane yielded 23.3 g (35.2 mmol, 86.9% based on C{1,8}): b.p.: 145–150° C. (0.1 torr), m.p.: 38° C. $^1$H NMR (C$_6$D$_6$) δ7.31 (m, 2 H), 6.89 (m, 2 H), 1.84 (m, 2 H), 0.75 (m, 2 H), −0.06 (s, 6 H, $^2$J$_{Si,H}$ 6.4 Hz). $^{13}$C{$^1$H} NMR (δ, C$_6$D$_6$): δ136.3, 135.6, 131.9, 125.0, 119.3 (tt, $^1$J$_{C,F}$=254 Hz, $^2$J$_{C,F}$=31.1 Hz), 118.0 (qt, $^1$J$_{C,F}$=288 Hz, $^2$J$_{C,F}$=33.0 Hz), 112.7, 112.7, 111.9, 111.9 (tm), 111.2 (tm), 109.1 (tm), 26.5 (t, $^2$J$_{C,F}$=23.8 Hz), 5.56 (s, $^1$J$_{C,Si}$=50.7 Hz), −3.65 (S, $^1$J$_{C,Si}$=53.1 Hz).

6. p-[{C$_x$F$_{2x+1}$(CH$_2$)$_2$}$_m$SiMe$_{3-m}$]C$_6$H$_4$Li (F{m,x}, m=0, 1; x=6, 8)

General Procedure

A solution of E{m,x} in n-hexane was treated either with 1 molar equivalent of n-BuLi (1.5 M solution in n-hexane) at 0° C. or with 2 molar equivalents of t-BuLi (1.5 M solution in n-hexane) at −78° C. The reaction mixture was allowed to reach room temperature and stirred over night. The voluminous white precipitate formed was separated, washed twice with 20 mL of n-hexane and dried in vacuo.

F{0}

4.67 g (20.4 mmol) of E{0} in 100 mL of n-hexane and 13.6 mL (20.4 mmol) of n-BuLi yielded 2.21 g (14.2 mmol, 69.6%) of product. 2.03 g (8.84 mmol) of E{0} and 11.8 mL (0.018 mmol) of t-BuLi afforded 1.8 g of a mixture of 1.15 g (7.32 mmol, 82.8%) of F{0} and LiBr. $^1$H NMR (C$_6$D$_6$): δ7.45 (m, 1H), 7.20 (m, 3 H), 0.19 (s, 9 H).

F{1,6}

6.1 g (10.9 mmol) of E{1,6} in 50 mL of n-hexane and 14.5 mL (21.7 mmol) of t-BuLi yielded 4.89 g (10.0 mmol, 91.7%) of product. $^1$H NMR (C$_6$D$_6$): δ7.27 (m, 1H), 7.16 (m, 3 H), 1.92 (m, 2 H), 0.83 (m, 2 H), 0.01 (s, 6 H).

F{1,8}

4.36 g (6.59 mmol) of E{1,8} in 30 mL of n-hexane and 4.39 mL (6.58 mmol) of n-BuLi yielded 2.74 g (4.66 mmol, 70.7%) of product. 9.28 g (14.0 mmol) of E{1,8} in 50 mL of n-hexane and 18.7 mL (28.1 mmol) of t-BuLi afforded 7.07 g of a mixture of 6.16 g (10.5 mmol, 75.0%) F{1,8} and LiBr. $^1$H NMR (C$_6$D$_6$): 7.27 (m, 1H), 7.17 (m, 3 H), 1.90 (m, 2 H), 0.83 (m, 2 H), 0.03 (s, 6 H).

7. P[C$_6$H$_4$-p-{SiMe$_{3-m}$(CH$_2$)$_2$C$_x$F$_{2x+1}$}$_m$]$_3$ (D{m,x}, m=0, 1; x=6, 8) through Method a)

General Procedure 3 equiv of F{m,x} were either suspended in n-pentane and cooled with ice water (x=6) or dissolved in a mixture of n-hexane and THF (5:1 (v/v)) at −78° C. One equivalent of PCl$_3$, or P(OMe)$_3$ were added slowly and one hour after the addition the cooling bath was removed. After being stirred over night the reaction mixture was filtered and all volatiles were removed in vacuo. The white residue was washed three times with 20 mL of n-pentane. The volume of the combined n-pentane phases was reduced to 10 mL and it was stored at −10° C. The solvent was decanted and the white precipitate was dried in vacuo.

D{0} has been prepared before using this route in U.S. Pat. No. 2,673,210, Frisch, K. C.; Lyons, H.; *J. Am. Chem. Soc.*, 1953, 75, 4078.

D{0}

1.8 of a mixture of F{0} and LiBr containing 7.36 mmol F{0} suspended in 40 mL of n-pentane and treated with 0.289 mL (2.45 mmol) of P(OMe)$_3$ yielded 1.06 g (2.21 mmol, 90% based on F{0}) as a yellow precipitate. Recrystallization from ethanol afforded pure white, crystalline D{0}. 0.68 g (4.33 mmol) of F{0} in 30 mL of n-hexane and 5 mL of THF were treated with 0.121 mL (1.44 mmol) of PCl$_3$ yielding 0.4 g (0.83 mmol, 57.5% based on F{0}) of D{0}; m.p.: 194° C. Anal. calcd for C$_{27}$H$_{39}$Si$_3$P: C 67.7, H 8.21, Si 17.6, P 6.47; found C 67.5, H 8.31, Si 17.8, P 6.58. $^1$H NMR (C$_6$D$_6$/C$_6$F$_6$ 1:1 (v/v)) δ7.35 (m, 2 H), 7.23 (m, 2 H), 0.28 (s, 9 H). $^{31}$P{$^1$H} NMR (C$_6$D$_6$/C$_6$F$_6$ 1:1 (v/v)): δ−4.61 (s). $^{29}$Si{$^1$H} NMR (C$_6$D$_6$/C$_6$F$_6$ 1:1 (v/v)): δ4.03. $^{13}$C{$^1$H} NMR (C$_6$D$_6$) δ141.3 (s, $^1$J$_{Si,C}$=64.7 Hz), 138.6 (d, $^1$J$_{P,C}$=12.2 Hz), 133.8 (d, $^3$J$_{P,C}$=6.6 Hz), 133.6 (d, $^2$J$_{P,C}$=18.9 Hz), −0.83 (s, $^1$J$_{Si,C}$=52.3 Hz).

D{1,6}

4.19 g (8.6 mmol) of F{1,6} in a mixture of 30 mL of n-hexane and 5 mL of THF was treated with 0.25 mL (2.84 mmol) of PCl$_3$ in 5 mL n-hexane. Yield 2.85 g (1.93 mmol, 67.3% based on F{1,6}); m.p.: 89° C. Anal. calcd for C$_{48}$H$_{42}$F$_{39}$Si$_3$P: C 39.1, H 2.85, F 50.3, Si 5.71, P 2.10. Found C 39.3, H 2.87, F 50.1, Si 5.80, P 2.08; $^1$H NMR (C$_6$D$_6$/C$_6$F$_6$, 1:1 (v/v)): δ7.33 (m, 2 H), 7.25 (m, 2 H), 2.04 (m, 2 H), 0.97 (m, 2 H), 0.26 (s, 6 H). $^{31}$P{$^1$H} NMR (C$_6$D$_6$/C$_6$F$_6$ 1:1 (v/v)): δ−4.66. $^{29}$Si{$^1$H} NMR (C$_6$D$_6$/C$_6$F$_6$ 1:1 (v/v)): δ−1.69. $^{19}$F NMR (C$_6$D$_6$): δ−81.4 (tt, J$_{F,F}$=9.7 Hz, J$_{F,F}$=2.5 Hz, 3 F), −115.8 (m, 2 F), −122.2 (m, 2 F), −123.2 (m, 2 F), −123.3 (m, 2 F), −126.5 (m, 2 F). $^{13}$C{$^1$H} NMR (C$_6$D$_6$): δ139.4 (d, $^1$J$_{P,C}$=12.7 Hz), 138.7 ($^1$J$_{Si,C}$=65 Hz), 134.3 (d, $^3$J$_{P,C}$=6.7 Hz), 134.1 (d, $^2$J$_{P,C}$=18.9 Hz), 119.3 (tt, $^1$J$_{C,F}$=254 Hz, $^2$J$_{C,F}$=30.5 Hz), 118.1 (qt, $^1$J$_{C,F}$=289 Hz, $^2$J$_{C,F}$=33.3 Hz), 112.3 (tquin, $^1$J$_{C,F}$=268 Hz, $^2$J$_{C,F}$=32.0 Hz), 112.1 (tquin, $^1$J$_{C,F}$=271 Hz, $^2$J$_{C,F}$=31.8 Hz), 111.3 (tquin, $^{11}$J$_{C,F}$=272 Hz, $^2$J$_{C,F}$=31.7 Hz), 109.4 (tqt, $^1$J$_{C,F}$=260 Hz, $^2$J$_{C,F}$=30.5 Hz), 26.6 (t, $^2$J$_{C,F}$=23.5 Hz) 5.62 (s, $^1$J$_{C,Si}$=50.9 Hz), −3.51 (s, $^1$J$_{C,Si}$=53.1 Hz). $^{13}$C{$^{19}$F}$^a$ NMR (C$_6$D$_6$): δ139.4 (dt, $^1$J$_{P,C}$=12.8 Hz), 138.6, 134.2 (dm), 119.3 (s), 118.1 (q, $^1$J$_{C,F}$=269 Hz), 112.3, 112.1, 111.3, 109.5 (q, $^2J_{C,F}$=25.1 Hz), 26.6 (tm, $^1J_{C,H}$=125 Hz), 5.57 (t, $^1J_{C,H}$=121 Hz), 4.34 (q, $^1J_{C,H}$=121 Hz).

D{1,8}

2.74 g (4.65 mmol) of F{1,8} in a mixture of 30 mL of n-hexane and 5 mL of THF was treated with 0.135 mL (1.55 mmol) of $PCl_3$ in 5 mL n-hexane. Yield: 1.59 g (0.89 mmol, 57% based on F{1,8}). 7.07 g of a mixture of F{1,8} and LiBr containing 10.5 mmol of F{1,8} was suspended in 100 mL of n-pentane was treated with 0.41 mL (3.48 mmol) of $P(OMe)_3$ yielding 4.00 g (2.25 mmol, 64.3% based on F{1,8}) m.p.: 101° C. Anal. calcd for $C_{54}H_{42}F_{51}Si_3P$: C 36.52, H 2.34, F 54.6, Si 4.74, P 1.75. Found: C 36.6, H 2.41, F 54.4, Si 4.85, P 1.86; $^1H$ NMR ($C_6D_6/C_6F_6$ 1:1 (v/v)): δ7.34 (m, 2 H), 7.25 (m, 2 H), 2.04 (m, 2 H), 0.98 (m, 2 H), 0.27 (s, 6 H). $^{31}P\{^1H\}$ NMR (δ, $C_6D_6/C_6F_6$ 1:1 (v/v)) −4.67. $^{29}Si\{^1H\}$ NMR ($C_6D_6/C_6F_6$ 1:1 (v/v)): δ−1.69. $^{13}C\{^{19}F\}^a$ NMR ($C_6D_6$): δ139.4 (dt, $^1J_{P,C}$=12.7 Hz , $^2J_{C,H}$=6.1 Hz), 138.6 (m), 134.3 (dm), 134.1 (dm) 119.3 (m), 118.1 (q, $^1J_{C,F}$=268 Hz), 112.3 (s), 112.2 (s), 111.8 (s), 111.7 (s), 111.1 (s), 109.3 (qm, $^2J_{C,F}$=26 Hz, 26.5 (tt, $^1J_{C,H}$=129 Hz, $^2J_{F,F}$= 5.5 Hz), 5.58 (t, $^1J_{C,H}$=121 Hz), −3.51 (q, $^1J_{C,H}$=119 Hz) $^{19}F$ NMR ($C_6D_6$): δ−81.4 (m, 3 F), −116.7 (m, 2 F), −122.2 (m, 6 F), −123.0 (m, 2 F), −123.7 (m, 2 F),−126.8 (m, 2 F).

8. Tris(p-bromophenyl)phosphine $P(C_6H_4$-p-$Br)_3$:

Slight variation of method described by Benassi, R.; Schenetti, M. L.; Taddei, F.; Vivarelli, P.; Dembech, P.; *J. Chem. Soc., Perkin Trans. II*, 1974, 1338; Ravindar, V.; Hemling, H.; Schumann, H.; Blum, J.; *Synthetic Communications*, 1992, 22, 841.

1,4-Dibromobenzene (20 g, 84.8 mmol) was dissolved in a mixture of 300 mL of n-hexane and 100 mL of diethyl ether, treated with 84.8 mmol (53 mL, 1.6 M) of n-BuLi and stirred for 5 minutes at room temperature. Before the addition of a solution of 2.46 mL (28.3 mmol) of $PCl_3$ in 40 mL of n-hexane the yellowish solution was cooled with a ethanol/dry ice bath for 20 minutes. The cooling bath was removed after 2 hours and the reaction mixture was stirred over night. The brownish mixture was quenched with 50 mL of a saturated $NH_4Cl$ solution in water. The aqueous phase was extracted two times with 20 mL of n-hexane. The combined organic phases were dried over $MgSO_4$ and all volatiles were removed in vacuo. The light yellow solid obtained was recrystalized from 30 mL of n-hexane. The pure phosphine was isolated as a white crystalline solid. Yield: 10 g (20.04 mmol, 70.8% based on $PCl_3$). $^1H$ NMR ($C_6D_6$): δ6.82 (m, 2 H), 7.15 (m, 2H); $^{31}P\{^1H\}$ NMR ($C_6D_6$): δ−7.98.

9. $P[C_6H_4$-p-$SiMe_{3-m}\{(CH_2)_2C_xF_{2x+1}\}m]_3$ (D{m,x}; m=0, 2, 3; x=6, 8) through Method b)

General Procedure $P(C_6H_4$-p-$Br)_3$ was dissolved in diethyl ether and treated with 6 equiv of t-BuLi (1.5 M in n-hexane) at −78° C. After 10 minutes, when a voluminous white precipitate was formed, a solution of the fluorous bromosilane (C{m,x}) in diethyl ether was added. The reaction mixture was allowed to reach room temperature and was stirred for another 15 h. In case the phosphines did not precipitate quantitatively the reaction mixture was filtered and the product was dried in vacuo. All volatiles of the filtrate were removed in vacuo and the residue extracted in 50 mL of FC-72. The remainder of the product was isolated from the filtrate by removal of the volatiles in vacuo. Minor amounts of impurities were removed by washing with n-pentane. D{0} has been prepared before using method a) (See example 7).

D{0}

0.27 mL (2.1 mmol) of $Me_3SiCl$, 0.35 g (0.70 mmol) of $P(C_6H_4$-p-$Br)_3$ in 60 mL diethyl ether and 2.47 mL (4.2 mmol) of t-BuLi solution yielded 0.33 g (0.684 mmol, 98% based on $SiMe_3Cl$).

D{1,6}

6.09 g (13.8 mmol) of C{1,6}, 2.30 g (4.61 mmol) of $P(C_6H_4$-p-$Br)_3$ in 50 mL of hexane/diethyl ether (3:1, v/v) and 18.4 mL (27.7 mmol) of t-BuLi solution yielded 5.23 g (3.53 mmol, 77% based on C{1,6}) after quenching with degassed water (20 mL), phase separation and extraction with diethylether (30 mL).

D{2,6}

9.43 g (11.6 mmol) of C{2,6} in 150 mL of diethyl ether, 2.09 g (4.19 mmol) of $P(C_6H_4$-p-$Br)_3$ in 100 mL of diethyl ether and 16.6 mL (24.9 mmol) of t-BuLi solution yielded 9.37 g (3.79 mmol, 98% based on C{2,6}). m.p.: 67° C. Anal. calcd for $C_{69}H_{45}F_{78}Si_3P$: C 33.50, H 1.82, F 59.97, Si 3.40, P 1.25. Found: C. 33.64, H 1.95, F 60.11, Si 3.32, P 1.22. $^1H$ NMR ($C_6D_6/C_6F_6$ 1:1 (v/v)): δ7.32 (m, 6 H), 7.28 (m, 6 H), 2.02 (m, 12 H), 1.01 (m, 12 H), 0.24 (s, 9 H). $^{31}P\{^1H\}$ NMR ($C_6D_6/C_6F_6$ 1:1 (v/v)): δ−4.62. $^{29}Si\{^1H\}$ NMR ($C_6D_6/C_6F_6$ 1:1 (v/v)): δ0.24. $^{19}F$ NMR ($C_6D_6/C_6F_6$ 1:1 (v/v)): δ−81.5 (m, 3 F), −116.0 (m, 2 F), −122.0 (m, 2 F), −123.0 (m, 2 F), −123.3 (m, 2 F), −126.4 (m, 2 F); $^{13}C\{^1H\}$ NMR ($C_6D_6/C_6F_6$ 1:1 (v/v)): δ139.0 (m), 138.3, 134.4 (dm), 119.4 (s), 118.5 (q, $^1J_{C,F}$=271 Hz), 112.6, 112.5, 111.7, 109.9, 26.6 (tm, $^1J_{C,H}$=130 Hz), 4.06 (t, $^1J_{C,H}$=120 Hz), −6.45 (q, $^1J_{C,H}$=120 Hz)

D{3,6}

16.4 g (14.3 mmol) of C{3,6} in 100 mL of diethyl, 2.38 g (4.77 mmol) of $P(C_6H_4$-p-$Br)_3$ in 100 mL of diethyl ether and 19.1 mL (28.6 mmol) of t-BuLi solution yielded 14.2 g (4.09 mmol, 86% based C{3,6}), m.p.: 50–55° C. Anal. calcd for $C_{90}H_{48}F_{117}Si_3P$: C. 31.2, H 1.40, F 64.1, Si 2.43, P 0.89. Found: C. 33.9, H 1.68, F 60.7, Si 2.66, P 0.96. $^1H$ NMR ($C_6D_6/C_6F_6$ 1:1 (v/v)): δ7.35 (m, 4H), 2.05 (m, 6H), 1.08 (m, 6H). $^{31}P\{^1H\}$ NMR ($C_6D_6/C_6F_6$ 1:1 (v/v)): δ−4.49. $^{29}Si\{^1H\}$ NMR ($C_6D_6/C_6F_6$ 1:1 (v/v)): δ1.25. $^{19}F$ NMR ($C_6D_6/C_6F_6$ 1:1 (v/v)): δ−81.5 (m, 3 F), −115.9 (m, 2 F), −121.9 (m, 2 F), −122.9 (m, 2 F), −123.2 (m, 2 F), −126.3 (m, 2 F).

D{2,8}

23.2 g (22.8 mmol) of C{2,8} in 130 mL of diethyl ether, 3.42 g (6.85 mmol) of $P(C_6H_4$-p-$Br)_3$ in 200 mL diethyl ether and 27.4 mL (41.1 mmol) of t-BuLi solution yielded 21.0 g (6.84 mmol, 90% based on C{2, 8}) m.p.: 72° C. Anal. calcd for $C_{81}H_{45}F_{102}Si_3P$: C. 31.65, H 1.46, F 63.10, Si 2.73, P 1.00. Found C 31.71, H 1.41, F 62.91, Si 2.72, P 1.08; $^1H$ NMR ($C_6D_6/C_6F_6$ 1:1 (v/v)): δ7.30 (m, 4H), 2.03 (m, 4 H), 1.02 (m, 4 H), 0.25 (s, 3 H). $^{31}P\{^1H\}$ NMR ($C_6D_6/C_6F_6$ 1:1 (v/v)): δ−4.70. $^{29}Si\{^1H\}$ NMR ($C_6D_6/C_6F_6$ 1:1 (v/v)): δ0.23. $^{13}C\{^{19}F\}^a$ NMR ($C_6D_{14}$/FC-72 1:1 (v/v)): δ140.4 (dt, $^1J_{P,C}$=14.0 Hz, $^2J_{C,H}$=6.7 Hz), 136.1 (m), 134.3 (dm), 119.0 (m), 118.4 (q, $^1J_{C,F}$=262 Hz), 112.4 (s), 112.3 (s), 112.0 (s), 111.4 (s), 109.8 (qm, $^2J_{C,F}$=26 Hz), 26.5 (tm, $^1J_{C,H}$=131 Hz), 3.98 (t, $^1J_{C,H}$=123 Hz), −6.98 (q, $^1J_{C,H}$=120 Hz). $^{19}F$ NMR ($C_6D_6/C_6F_6$ 1:1 (v/v)): δ−82.4 (m, 3 F), −117.0 (m, 2 F), −122.8 (m, 6 F), −123.7 (m, 2 F), −124.1 (m, 2 F), −127.2 (m, 2 F).

D{3,8}

17.2 g (11.9 mmol) of C{2,8} in 200 mL of diethyl ether, 1.78 g (3.57 mmol) of $P(C_6H_4$-p-$Br)_3$ in 200 mL diethyl ether and 14.2 mL (21.4 mmol) of t-BuLi solution yielded 15.3 g (3.50 mmol, 88% based on C{3,8}); m.p.: 124° C. Anal. calcd for $C_{108}H_{48}F_{153}Si_3P$: C. 29.67, H 1.10, F 66.56, Si 1.92, P 0.71. Found: C. 29.66, H 1.15, F 66.38, Si 1.96, P 0.74; $^1H$ NMR ($C_6D_6/C_6F_6$ 1:1 (v/v)): δ7.35 (m, 4 H), 2.07 (m, 6 H), 1.09 (m, 6 H). $^{31}P\{^1H\}$ NMR ($C_6D_6/C_6F_6$ 1:1 (v/v)): δ−4.49 (s). $^{29}Si\{^1H\}$ NMR ($C_6D_6/C_6F_6$ 1:1 (v/v)):

δ1.24. $^{19}$F NMR (C$_6$D$_6$/C$_6$F$_6$ 1:1 (v/v)): δ−80.9 (m, 3 F), −115.4 (m, 2 F), −121.4 (m, 6 F), −122.3 (m, 2 F), −122.6 (m, 2 F), −125.8 (m, 2 F).

10. Solubility Studies

Saturated solutions in the appropriate solvent were prepared by stirring a suspension of the fluorous phosphine for 2 hours at 25° C. A sample (3.000±0.002 mL) was taken after allowing the solution to settle. The total weight of the saturated solution was determined. All solvent was removed in vacuo (0.1 mbar, for 15 h) upon which the weight was constant within ±0.001 g and the weight of the residue was determined.

11. Determination of Partition Coefficients

The partition coefficients were determinded by dissolving a known amount of phosphine (typically between 11 and 60 µmol) in a fluorous biphasic system either consisting of c-C$_6$F$_{11}$CF$_3$ (2.000±0.002 mL) and n-pentane, n-octane or toluene (2.006±0.002 mL). The resulting mixture was stirred at 25° C. until all solid had dissolved and equilibrated in a water ice bath (1 h). An aliquot (0.500±0.002 mL) was removed from each layer by syringe. Analysis by ICP-AAS on phosphorus gave the amount of phosphine present, with an accuracy of ±0.3 ppm. A conservative estimate of the experimental error in the partition coefficient is ±1 in the last digit.

12. Bis(bis-4-bromophenylphosphino)ethane p-Dibromobenzene (22.5 g, 95.3 mmol) was dissolved in a mixture of 300 ml of n-hexane and 100 ml of ether. To this solution 58.1 ml of a 1.64 M (95.3 mmol) n-BuLi solution in pentane was added. After stirring for 5 minutes, the mixture was cooled to −78° C. followed by stirring for another 20 minutes. To the white suspension 5.53 g (23.8 mmol) of bis(dichlorophosphino)ethane was added. The cooling bath was removed after two hours. After stirring the reaction mixture overnight, 20 ml of saturated aqueous NH$_4$Cl-solution was added and the two layers were separated. The aqueous layer was extracted twice with 50 ml CH$_2$Cl$_2$ and the collected organic layers were dried on MgSO$_4$. After filtration, the solvents were evaporated in vacuo, which yielded 14.46 g of yellow-white solid (85%). Anal calcd. for C$_{26}$H$_{20}$Br$_4$P$_2$: C. 43.74, H 2.82, P 8.68. Found: C. 43.82, H 3.01, P 8.56; $^1$H-NMR (CDCl$_3$): δ1.98 (4H, m), 7.12 (8H, m), 7.43 (8H, d); $^{31}$P-NMR (CDCl$_3$): δ−13.8 (s)

13. p-Silyl substituted dppe derivatives G{m,x}

General Procedure

Bis(bis(4-bromophenyl)phosphino)ethane was dissolved in THF and cooled to −90° C. in an ethanol/liquid nitrogen bath. To this solution 8 equivalents of t-BuLi in pentane were added. The reaction mixture was stirred for 30 minutes, while the temperature was kept below −60° C. The green suspension was treated with 4 equivalents of silyl halide and the resulting solution was stirred below −60° C. for 1 hour. The yellowish solution, thus formed, was warmed very slowly to room temperature. In case of G{0} and G{1,6}, after evaporating all solvents in vacuo, the white solid was dissolved in degassed water/CH$_2$Cl$_2$. The organic layer was separated, dried on MgSO$_4$, filtrated and evaporated to dryness. The products were isolated as white solids. In case of G{2,6} and G{3,6}, the residue obtained after evaporating the solvent in vacuo was dissolved in a two-phase system consisting of 10 ml of methanol and 10 ml of FC-72. The fluorous layer was separated and dried, resulting in a clear yellow oil. The compound was further purified by Kugelrohr G{2,6} or washing with pentane G{3,6}.

G{0}

A solution of 1.26 g (1.76 mmol) of bis(bis(4-bromophenyl)phosphino)ethane in THF 9.4 ml (14.1 mmol) of t-BuLi solution and 0.80 g (7.06 mmol) of Me$_3$SiCl yielded 1.10 g of a white solid (91%); Anal. calcd. for C$_{38}$H$_{56}$P$_2$Si$_4$: C 66.42, H 8.21, P 9.01. Found: C. 66.51, H 8.28, P 9.06; $^1$H-NMR (CDCl$_3$): δ0.25 (s, 6H), 2.13 (ps t, 4H), 7.30 (m, 8H), 7.44 (d, 8H); $^{31}$P-NMR (CDCl$_3$): δ−11.9 (s).

G{1,6}

A solution of 0.87 g (1.22 mmol) of bis(bis(4-bromophenyl)phosphino)ethane in THF 6.5 ml (9.8 mmol) of t-BuLi solution and 2.26 g (5.12 mmol) of C{1,6}, yielded 2.08 g of white solid (85%); Anal. calcd. for C$_{66}$H$_{60}$F$_{52}$P$_2$Si$_4$: C. 39.33, H 3.00, P 3.07. Found: C. 39.40, H 3.09, P 2.88; $^1$H-NMR (C$_6$D$_6$/C$_6$F$_6$, 1:1 (v/v)): δ0.25 (24 H, s), 0.96 (m, 8H), 2.01 (m, 8H), 2.12 (ps t, 4H), 7.22 (m, 8H), 7.29 (d, 8H); $^{31}$P-NMR (C$_6$D$_6$/C$_6$F$_6$ 1:1 v:v): δ−11.7; $^{19}$F-NMR (C$_6$D$_6$/C$_6$F$_6$, 1:1 (v/v)): δ−128.2 (m, 2F), −125.1 (m, 2F), −124.9 (m, 2F), −124.0 (m, 2F), −117.9 (m, 2F), −82.8 (t, 3F).

G{2,6}

A solution of 1.20 g (1.68 mmol) of bis(bis(4-bromophenyl)phosphino)ethane in THF 9.0 ml (13.5 mmol) of t-BuLi solution and 6.7 g of C{2,6} yielded 4.91 g of a colorless oil (87%); Anal. calcd. for C$_{94}$H$_{64}$F$_{104}$P$_2$Si$_4$: C. 33.77, H 1.93, P 1.85. Found: C. 33.71, H 1.83, P 1.82; $^1$H-NMR (C$_6$D$_6$/C$_6$F$_6$, 1:1 (v/v)): δ0.18 (s, 12H), 0.96 (m, 16H), 2.01 (m, 20H), 7.25 (m, 16H); $^{31}$P-NMR (C$_6$D$_6$/C$_6$F$_6$, 1:1 (v/v)): δ−11.4 (s)

G{3,6}

A solution of 0.47 g (0.66 mmol) of bis(bis(4-bromophenyl)phosphino)ethane in THF 3.5 ml (5.3 mmol) of t-BuLi solution and 3.58 g of C{3,6} yielded 1.60 g of a yellow oil (55%); Anal calcd. for C$_{122}$H$_{68}$F$_{156}$P$_2$Si$_4$: C. 31.37, H 1.47, P 1.33. Found: C. 31.46, H 1.38, P 1.44; $^1$H-NMR (C$_6$D$_6$/C$_6$F$_6$, 1:1 (v/v)): δ1.01 (m, 24H), 1.95 (m, 28H), 7.23 (m, 16H); $^{31}$P-NMR (C$_6$D$_6$/C$_6$F$_6$, 1:1 (v/v)): δ−11.4 (s)

G{1,8}

A solution of 1.15 g (1.61 mmol) of bis(bis(4-bromophenyl)phosphino)ethane in THF 8.6 ml (12.9 mmol) of t-BuLi solution and 3.49 g (6.45 mmol) of C{1,8} afforded a light brown solid which was washed with with degassed water, acetone and dried in vacuo. Yield: 74%; Anal calcd for C$_{74}$H$_{60}$F$_{68}$P$_2$Si$_4$: C. 36.80, H 2.50, P 2.56. Found: C. 36.65, H 2.59, P 2.48; $^1$H NMR (C$_6$D$_6$/C$_6$F$_6$, 1:1 (v/v)): δ0.23 (s, 24 H), 0.94 (m, 8H), 2.03 (m, 8H), 2.12 (ps t, 4H), 7.23 (m, 8H), 7.30 (d, 8H); $^{31}$P NMR (C$_6$D$_6$/C$_6$F$_6$, 1:1 (v/v)): δ−11.3 (s); $^{19}$F NMR (C$_6$D$_6$/C$_6$F$_6$, 1:1 (v/v)): δ−127.6 (m, 2F), −124.4 (m, 2F), −124.0 (m, 2F), −123.2 (m, 6F), −117.4 (m, 2F), −82.8 (t, 3F)

14. (D{0})$_3$RhCl (H{0})

1.436 g (2.999 mmol) of D{0} and 0.177 g (0.359 mmol) of [(COD)RhCl]$_2$ were dissolved in a mixture of 20 mL of n-hexane and 5 mL of toluene. After stirring for 15 h all volatiles were removed in vacuo. The orange residue was dissolved in 10 mL of n-hexane, while warming up the mixture to ~40° C. The solution was stored at −10° C. for 12 h. The precipitate was filtered off and the solution stored for 3 days at −10° C. Again, the precipitate was filtered off and all volatiles of the solution were removed in vacuo. 0.657 g (0.417 mmol, 58.1% based on Rh) of H{0} were obtained as an orange solid. Anal. calcd for C$_{81}$H$_{117}$ClSi$_9$P$_3$Rh: C. 61.78, H 7.49, Si 16.05, P 5.90. Found: C. 61.65, H 7.56, Si 15.83, P 5.94; $^1$H NMR (C$_6$D$_6$): δ7.9 (m, 18 H), 7.2 (m, 18 H), 0.18 (m, 81H). $^{13}$C{$^1$H} NMR (C$_6$D$_6$): δ141.3 (s), 141.0

(s), 137.1 (m), 135.5 (m), 134.7 (d), 133.8 (d), 132.7 (m), 132.1 (d) −0.75 (s, $^1J_{C,Si}$=52.5 Hz).

15. (D{1,6})$_3$RhCl (H{1,6})

3.210 g (2.176 mmol) of D{1,6} dissolved in a mixture of 20 mL of n-hexane and 5 mL of toluene was treated with 0.179 g (0.363 mmol) of [(COD)RhCl]$_2$ at 25° C. After stirring for 15 h the volume of the solution was reduced by ⅔ and toluene was added (20 mL). Stirring was continued for 15 min affording a biphasic system. The upper phase was carefully decanted. The fluorous phase consisting of a dark red oil was washed two times with toluene (10 mL) and pre dried in vacuo (0.1 bar). Further drying in high vacuum (10$^{-6}$ bar) for 12 hours afforded 1.50 g of a highly viscous dark red oil containing H{1,6} (0.318 mmol, 43.8% based on Rh) and 0.1 equiv of D{1,6}. Anal. calcd for C$_{144}$H$_{126}$F$_{117}$ClSi$_9$P$_3$Rh: C. 37.9, H 2.78, F 48.71, Si 5.54, P 2.04. Found: C. 37.76, H 2.85, F 48.48, Si 5.61, P 2.11; $^1$H-NMR (FC-72/C$_6$D$_6$, 1:1 (v/v)): δ7.61 (m, 18 H), 6.97 (m, 18 H), 1.87 (m, 18 H) 0.80 (m, 18 H) 0.04 (m, 54 H).

16. (D{1,8})$_3$RhCl (H{1,8})

Method 1: 2.801 g (1.578 mmol) of D{1,8} dissolved in 60 mL of benzene was treated with 0.130 g (0.263 mmol) of [(COD)RhCl]$_2$ at 25° C. After stirring for 15 h, when a waxy, yellow precipitate was observed, the reaction mixture was treated with c-C$_6$F$_{11}$CF$_3$ (10 mL). The color of the fluorous phase turned to dark red, while the organic upper phase remained yellow. After phase separation the fluorous phase was washed two times with 10 mL of benzene and all volatiles were removed in vacuo (0.1 bar). Further drying of the remaining dark red oil in high vacuum (10$^{-6}$ bar) for 12 h yielded 2.497 g (0.457 mmol, 86.9% based on Rh) of a highly viscous dark red oil being pure H{1,8}.

Method 2

0.914 g (0.515 mmol) of D{1,8} and 0.158 g (0.171 mmol) of RhCl(PPh$_3$)$_3$ were dissolved in 20 mL of benzene at 25° C. Instantly a dark red oil precipitated. 2.5 mL of c-CF$_3$C$_6$F$_{12}$ was added, when the formation of a dark red bottom layer and an orange upper layer was observed. The upper layer was decanted and. all volatiles of the lower layer were removed in vacuo. The remaining red oil was further dried in high vacuum (10$^{-6}$ bar, 12 h). 0.690 g of a highly viscous dark red oil containing 0.119 mmol of H{1,8} (69.6% based on Rh) and 0.15 equiv of D{1,8} was obtained. Anal. calcd for C$_{162}$H$_{126}$F$_{153}$ClSi$_9$P$_3$Rh: C. 35.61, H 2.32, F 53.20, Si 4.63, P 1.70, Found: C. 35.74, H 2.37, F 53.03, Si 4.66, P 1.65. $^1$H NMR (CF$_3$C$_6$F$_{14}$/C$_6$D$_{14}$, 1:1 (v/v)): δ7.43 (m, 18 H), 7.00 (m, 18 H), 1.89 (m, 18 H), 0.85 (m, 18 H), 0.15 (m, 54 H). $^{13}$C{$^1$H} NMR (CF$_3$C$_6$F$_{14}$/C$_6$D$_{14}$, 1:1 (v/v)): δ138.7 (s), 138.4 (s), 137.0 (s), 135.3 (s), 134.7 (s), 132.4 (s), 128.7 (s), 126–102 (m), 26.4 (t, $^2J_{C,F}$=23.8 Hz), 5.51 (s), −4.35 (s, $^1J_{C,Si}$=52.6 Hz).

17. [Rh(COD) (G{1,6}]BPh$_4$ (I{1,6})

A THF solution of 0.82 g (0.41 mmol) of the diphosphine G{1,6} was slowly added to a THF solution containing 128 mg (0.41 mmol) of [Rh(COD) (Acac)] (Acac=acetylacetonate anion) and 0.28 g (0.82 mmol) of NaBPh$_4$. After stirring for 10 minutes the solvent was removed in vacuo. To the residue 10 ml of CH$_2$Cl$_2$ was added. A pure orange compound was obtained after filtration and drying in vacuo. Yield: 0.76 g (0.30 mmol, 73%). Anal. calcd for C$_{98}$H$_{92}$BF$_{52}$P$_2$RhSi$_4$: C. 46.43, H 3.66, P 2.44. Found: C. 46.05, H 3.70, P 2.62; $^1$H NMR (CDCl$_3$): δ0.38 (s, 24H), 1.02 (m, 8H), 2.10 (m, 20H), 4.93 (m, 4H), 6.76 (m, 4H), 6.86 (m, 8H), 7.30 (m, 8H), 7.44 (m, 8H), 7.60 (m, 8H); $^{31}$P NMR (CDCl$_3$): δ56.1 (d, $^1J_{RhP}$=148.4 Hz)

18. G{2,6}NiCl$_2$ (J{2,6})

In 100 mL of a 1:1 (v/v) mixture of ethanol and CF$_3$C$_6$H$_5$, 2.29 g (0.69 mmol) of G{2,6} was dissolved. The solution was slowly added to a solution of 163 mg (0.69 mmol) of NiCl$_2$.6H$_2$O in ethanol (10 mL). After evaporating all solvents in vacuo, the remaining red waxy solid was washed with ethanol and pentane and dried in vacuo. Yield: 2.13 g (0.61 mmol, 89%) Anal. calcd for C$_{94}$H$_{64}$Cl$_2$F$_{104}$NiP$_2$Si$_4$: C. 32.51, H 1.86, P 1.78. Found: C. 32.38, H 1.94, P 1.88. $^1$H NMR (FC-72/C$_6$D$_6$): δ8.03 (br, lw$_{1/2}$=56 Hz, 8H), 7.24 (br, lw$_{1/2}$=47 Hz, 8H), 1.90 (br, lw$_{1/2}$=52 Hz, 20H), 0.83 (br, lw$_{1/2}$=28 Hz, 16H), 0.043 (br, lw$_{1/2}$=17 Hz, 12 H). $^{31}$p NMR (FC-72/C$_6$D$_6$): δ55.7.

19. (G{m,6})PtCl$_2$ (K{m,6}, m=1, 2)

One equivalent of diphosphine G{m,6} dissolved in CH$_2$Cl$_2$ was added to a CH$_2$Cl$_2$-solution of Pt(COD)Cl$_2$. After stirring overnight, all solvent was removed in vacuo. PtCl$_2$(G{1,6})

Addition of 0.45 g (0.22 mmol) of G{1,6} to 84 mg (0.22 mmol) of Pt(COD)Cl$_2$ yielded 0.46 g (0.20 mmol, 93%) of a white solid. Anal calcd for C$_{66}$H$_{60}$Cl$_2$F$_{52}$P$_2$PtSi$_4$: C 34.75, H 2.65, P 2.72; found C 34.61, H 2.70, P 2.80; $^1$H-NMR (CDCl$_3$): δ0.34 (24 H, s), 1.00 (8H, m), 2.02 (8H, m), 2.36 (4H, m), 7.56 (8H, m), 7.85 (8H, m); $^{31}$P NMR (CDCl$_3$) 41.9 ($^1J_{PtP}$=3604 Hz).

PtCl$_2$(G{2,6})

0.41 g (0.12 mmol) of G{2,6} and 46 mg (0.12 mmol) of Pt(COD)Cl$_2$ yielded 0.39 g (0.11 mmol, 91%) of a light yellow solid. $^{31}$P NMR (CDCl$_3$/CF$_3$C$_6$H$_5$ 1:1 (v/v)): δ42.0 ($^1J_{PtP}$=3593 Hz).

20. Rhodium Catalyzed Hydrogenation Reactions

The catalytic experiments were carried out in a 30 mL Schienk flask, under dihydrogen atmosphere (1 bar). The catalyst was either dissolved in a hydrogen saturated toluene or perfluoro solvent and the mixture was stirred with a magnetic stirring bar (900 rpm). The olefinic substrate was added after initial dihydrogen uptake had ceased. The dihydrogen uptake was monitored using two mineral oil filled gas burettes. During the hydrogenation reactions one burette was opened to the reaction vessel while the other was recharged with dihydrogen. Results are lsited in Table 5.

Recycling Experiments

Only catalysts prepared through method 1 were used. Catalytic reactions were carried out under single phase fluorous conditions in c-CF$_3$C$_6$F$_{11}$ (2 mL) at 80° C. After >90% conversion (monitored by the H$_2$ uptake) the homogeneous reaction mixture was cooled to 0° C. and the upper organic layer was siphoned of. In between cycles the fluorous layer was kept under H$_2$ atmosphere. By warming up to 80° C. and addition of a fresh portion of 1-octene (12.74 mmol) a new cycle was started. The organic phases resulting from the first cycle were analyzed by GC and ICP-AAS. Results are listed in Table 5.

Experiments in CF$_3$C$_6$H$_5$

Catalytic reactions were carried out under single phase conditions in CF$_3$C$_6$H$_5$ at 80° C. under 1 bar of hydrogen pressure. After >90% conversion (monitored by the H$_2$ uptake) volatiles were distilled off and analyzed by GC. Activities (TOF) were determined for 25% conversion. Results are listed in Table 7.

21. Nickel Catalysed Cross-coupling in a Fluorous Biphasic Solvent System

In 2.5 ml of c-CF$_3$C$_6$F$_{11}$, 88 mg (17 μmol) of J{2,6} was dissolved. To this solution, 0.24 ml (2.4 mmol) of chlorobenzene, a known amount (ca 350 mg) of n-decane (as internal standard) and 2.5 ml of a 1.1 M (2.8 mmol) butyl magnesium bromide solution in di-n-butyl ether were added. The reaction mixture was stirred at 90° C. for 20 hours. After cooling to room temperature, the biphasic mixture was filtered and the two phases were separated. The organic layer was quenched with 3 ml of HCl (aq) (4 M) and filtered over MgSO$_4$. Conversions were determined by GC. A new cycle was started by adding substrate, Grignard solution and internal standard to the fluorous layer and the above procedure was repeated. Results are listed in Table 8.

What is claimed is:

1. A fluorous phosphine wherein at least one phosphorus atom is coupled to at least one aryl or alkyl moiety, to which moiety a fluorous tail is coupled, wherein a spacer group, containing a non-carbon atom, is positioned between the aryl or alkyl moiety and the fluorous tail, wherein the fluorous tail is a C$_x$F$_{2x+1}$ group, wherein x is an integer from 1 to 30; and wherein the non-carbon atom and is Si, Sn or Ge.

2. A fluorous phosphine according to claim 1, wherein the phosphine is a monophosphine or a diphosphine.

3. A fluorous phosphine according to claim 1, wherein the aryl moiety is a phenylene with or without a one or more additional substituents.

4. A fluorous phosphine according to claim 1, wherein the spacer group in the phosphine is

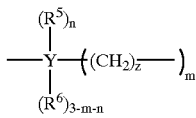

wherein Y is the non-carbon atom; R$^5$, R$^6$ is —C$_1$–C$_{14}$ alkyl, —C$_3$–C$_{14}$-cycloalkyl, —C$_1$–C$_{14}$-aryl, —C$_3$–C$_{14}$-arcycloalkyl, —C$_3$–C$_{14}$-cycloalkylaryl and/or fluorous tails, m is an integer from 1 to 3, n is an integer from 0 to 2 3, wherein the sum of m and n is smaller than or equal to 3, and z is an integer from 0 to 10.

5. A fluorous phosphine according to claim 1, wherein the phosphine is a monophosphine of the formula P(R$^1$)(R$^2$)(R$^3$), wherein at least one of R$^1$, R$^2$ and R$^3$ is an alkyl-R$^4$ or aryl-R$^4$, with or without one or more additional substituents, and wherein R$^4$ is the spacer group coupled to the fluorous tail.

6. A fluorous phosphine according to claim 1, wherein the phosphine is a diphosphine of the formula (R$^1$)(R$^2$)P—Z—P(R$^3$)(R$^7$), wherein Z is an achiral or chiral bridging hydrocarbyl moiety and wherein at least one of the groups R$^1$, R$^2$, R$^3$, or R$^7$ is an alkyl-R$^4$ or aryl-R$^4$ with or without one or more additional substituents, and wherein R$^4$ is the spacer group coupled to the fluorous tail.

7. A fluorous phosphine according to claim 1, wherein R$^5$ and/or R$^6$ is C$_1$–C$_6$-alkyl.

8. A fluorous phosphine according to claim 4, wherein R$^5$ and/or R$^6$ are different or identical fluorous tails.

9. A fluorous phosphine according to claim 4, wherein the phosphine is a fluorous monophosphine wherein at least one of R$^1$, R$^2$, R$^3$, is an aryl-R$^4$ with or without a substitutent, or a fluorous diphosphine, wherein at least one of R$^1$, R$^2$, R$^3$ or R$^7$ is an aryl-R$^4$ with or without a substitutent.

10. A fluorous phosphine according to claim 1, wherein Y is Si.

11. A process for the preparation of fluorous monophosphines wherein at least one phosphorus atom is coupled to at least one aryl or alkyl moiety, to which moiety a fluorous tail is coupled, wherein a spacer group, containing a non-carbon atom, is positioned between the aryl or alkyl moiety and the fluorous tail, wherein the fluorous tail is a C$_x$F$_{2x+1}$ group, wherein x is an integer from 1 to 30; and wherein the non-carbon atom and is Si, Sn or Ge comprising:

a) metallating X(CH$_2$)$_2$C$_x$F$_{2x+1}$;
b) reacting the metallated product obtained in step (a) with HY(X)$_{m(R^5)_n}$(R$^6$)$_{3-m-n}$;
c) reacting the compound obtained in step (b) with X$_2$;
d) mono-metallating a dihaloaryl compound with or without one or more additional substituents and reacting this mono-metallated compound with the compound obtained through steps (a)–(c);
e) metallating the compound obtained in step (d); and
f) reacting the metallated compound obtained in step (e) with a trivalent phosphorus compound containing one or more P—X' bonds, wherein X is a halogen or pseudohalogen; X' is a halogen or pseudohalogen, alkoxy, aryloxy, amido, triflato or aryl leaving group, and Ar is aryl.

12. A process for the preparation of fluorous diphosphines wherein at least one phosphorus atom is coupled to at least one aryl or alkyl moiety, to which moiety a fluorous tail is coupled, wherein a spacer group, containing a non-carbon atom, is positioned between the aryl or alkyl moiety and the fluorous tail, wherein the fluorous tail is a C$_x$F$_{2x+1}$ group, wherein x is an integer from 1 to 30; and wherein the non-carbon atom and is Si, Sn or Ge comprising the following steps:

a) reacting (X')$_2$P—Z—P(X')$_2$ with mono metallated ArX$_2$;
b) metallating the (XAr)$_2$P—Z—P(ArX)$_2$ compound obtained in step (a); and
c) reacting the metallated compound obtained in (b) with R$^4$X;

wherein Z is a bridging hydrocarbyl moiety, X is a halogen, X' is selected from the group consisting of a halogen, pseudo halogen, alkoxy, aryloxy, amido, triflato and aryl leaving group, and R$^4$ is the spacer group coupled to the fluorous tail.

13. A metal complex comprising a metal and at least one phosphine according to claim 1.

14. A metal complex according to claim 13 wherein the metal is selected from the group consisting of a rhodium, platinum, palladium, nickel, iron, ruthenium, osmium, cobalt and iridium.

15. A metal complex according to claim 13 wherein the metal complex is a catalyst-or catalyst precursor.

16. A catalytic system comprising the metal complex according to claim 13.

17. A method of catalyzing a chemical reaction in a fluorous phase process or fluorous biphasic process with a metal complex comprising a metal and at least one fluorous phosphine wherein at least one phosphorus atom is coupled to at least one aryl or alkyl moiety, to which moiety a fluorous tail is coupled, wherein a spacer group, containing a non-carbon atom, is positioned between the aryl or alkyl moiety and the fluorous tail, wherein the fluorous tail is a C$_x$F$_{2x+1}$ group, wherein x is an integer from 1 to 30; and wherein the non-carbon atom and is Si, Sn or Ge comprising contacting the metal complex with reactants of the chemical reaction, thereby catalyzing the reaction.

18. A method according to claim 17, wherein the chemical reaction is selected from the group consisting of hydroformylation, hydroboration, cross-coupling, a Heck-type reaction, hydrogenation of unsaturated compounds, and combinations thereof.

19. A process for the preparation of fluorous monophosphines wherein at least one phosphorus atom is coupled to at least one aryl or alkyl moiety, to which moiety a fluorous tail is coupled, wherein a spacer group, containing a non-carbon atom, is positioned between the aryl or alkyl moiety and the fluorous tail, wherein the fluorous tail is a $C_xF_{2x+1}$ group, wherein x is an integer from 1 to 30; and wherein the non-carbon atom and is Si, Sn or Ge comprising:

a) metallating $X(CH_2)_zC_xF_{2x+1}$;
b) reacting the metallated product obtained in step (a) with $Hy(X)_m(R^5)_n(R^6)_{3-m-n}$;
c) reacting the compound obtained in step (b) with $X_2$; and
d) reacting the compound obtained through steps (a)–(c) with tri-metallated phosphine obtained from $P(ArX)_3$ by halogen metal-exchange;

wherein X is halogen or pseudohalogen; and Ar is aryl.

20. The process according to claim 19 wherein X' is selected from the group consisting of Cl, OMe, OEt, $NMe_2$ and $NEt_2$.

21. A process for the preparation of fluorous monophosphines wherein at least one phosphorus atom is coupled to at least one aryl or alkyl moiety, to which moiety a fluorous tail is coupled, wherein a spacer group, containing a non-carbon atom, is positioned between the aryl or alkyl moiety and the fluorous tail, wherein the fluorous tail is a $C_xF_{2x+1}$ group, wherein x is an integer from 1 to 30; and wherein the non-carbon atom and is Si, Sn or Ge comprising:

a) reacting $CH_2=CH(CH_2)_zC_xF_{2x+1}$ with $HY(X)_m(R^5)_n(R^6)_{3-m-n}$;
b) mono-metallating a dihaloarene compound with or without one or more additional substituents and reacting this mono-metallated compound with the compound obtained in step (a);
c) metallating the compound obtained in step (b); and
d) reacting the metallated compound obtained in step (c) with a trivalent phosphorus compound containing one or more P—X' bonds, wherein X is a halogen or pseudohalogen, X' is a halogen, pseudohalogen, alkoxy, aryloxy, amido, triflato or aryl leaving group.

22. A process for the preparation of fluorous monophosphines wherein at least one phosphorus atom is coupled to at least one aryl or alkyl moiety, to which moiety a fluorous tail is coupled, wherein a spacer group, containing a non-carbon atom, is positioned between the aryl or alkyl moiety and the fluorous tail, wherein the fluorous tail is a $C_xF_{2x+1}$ group, wherein x is an integer from 1 to 30; and wherein the non-carbon atom and is Si, Sn or Ge comprising:

a) reacting $CH_2=CH(CH_2)_zC_xF_{2x+1}$ with $HY(X)_m(R^5)_n(R^6)_{3-m-n}$; and
b) reacting the compound obtained in step (a) with tri-metallated phosphine obtained from $P(ArX)_3$ by halogen metal-exchange; wherein X is a halogen or pseudohalogen; and Ar is aryl.

23. A process according to claim 12 wherein X' is selected from the group consisting of Cl, OMe, OEt, $NMe_2$ and $NEt_2$.

* * * * *

UNITED STATES PATENT AND TRADEMARK OFFICE
CERTIFICATE OF CORRECTION

PATENT NO. : 6,458,978 B1
DATED : October 1, 2002
INVENTOR(S) : Richter et al.

It is certified that error appears in the above-identified patent and that said Letters Patent is hereby corrected as shown below:

Column 3,
Lines 6-7, now reads "FIG. 1. Reagents: (i) 1.5 $HSiMe_2Cl$, catalyst: $H_2PtCl_6$ (aq); (ii) Excess of Mg; (iii) $HSi(Me_{3-m})Cl_m$; (iv) $Br_2$." should read -- FIG. 1. Reagents: (i) Excess of Mg; (ii) $HSi(Me_{3-m}) Cl_m$; (iii) $Br_2$; (iv) 1.5 $HSiMe_2Cl$, catalyst: $H_2PtCl_6$(aq). --

Column 11,
After line 33, before "EXAMPLES" should read:

TABLE 8

Results of Fluorous Biphasic Nickel-Catalysed Cross-Coupling after 20 h using (G{2, 6}) $NiCl_2$ (1 mol %) as Catalyst

| Cycle | Yield of Butylbenzene (%) |
|---|---|
| 1 | 91 |
| 2 | 28 |
| 3 | 8 |

Column 13,
Line 10, now reads "(tm, TC, H = 127 Hz)," should read -- (tm, $^1J_{C,H}$ = 127 Hz), --
Line 18, now reads "(d, $^3J$ = 3.8Hz, 3 H)." should read -- (d, $^3J_{H,H}$ = 3.8 Hz, 3 H). --
Lines 45-46, now reads "$^1$H NMR (6, $CDCl_3$)" should read -- $^1$H NMR ($\delta$, $CDCl_3$) --
Line 59, now reads "(1.44g, 10.7 mnmol)" should read -- (1.44g, 10.7 mmol) --

Column 14,
Line 28, now reads "(tquin, $^2J_{C,F}$ = 272 Hz, $^2J_{C,F}$ = 31.7 Hz)," should read -- (tquin, $^1J_{C,F}$ = 272 Hz, $^2J_{C,F}$ = 31.7 Hz), --

Column 15,
Line 13, now reads "5.0 9 (17.7 mmol)" should read -- 5.0 g (17.7 mmol) --

Column 16,
Line 11, now reads "$P[C_6H_4\text{-}p\text{-}\{SiMe_{3-m}(CH_2)_2C_xF_{2x+1}\}_{ml]3}$" should read -- $P[C_6H_4\text{-}p\text{-}\{SiMe_{3-m}(CH_2)_2C_xF_{2x+1}\}_m]_3$ --
Line 29, now reads "1.8 of a mixture" should read -- 1.8g of a mixture --
Line 63, now reads "$^{11}J_{C,F}$= 272 Hz," should read -- $^1J_{C,F}$= 272 Hz, --

UNITED STATES PATENT AND TRADEMARK OFFICE
CERTIFICATE OF CORRECTION

PATENT NO. : 6,458,978 B1
DATED : October 1, 2002
INVENTOR(S) : Richter et al.

It is certified that error appears in the above-identified patent and that said Letters Patent is hereby corrected as shown below:

Column 24,
Line 1, now reads "$X(CH_2)_2C_xF_{2x+1}$" should read -- $X(CH_2)_zC_xF2_{2x+1}$ --
Line 3, now reads "with $HY(X)_{m(R^5)}{}_n(R^6)_{3-m-n}$;" should read
-- with $HY(X)_m(R^5)_n(R^6)_{3-m-n}$; --

Signed and Sealed this

Twelfth Day of August, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,458,978 B1
DATED : October 1, 2002
INVENTOR(S) : Richter et al.

Figure 4:
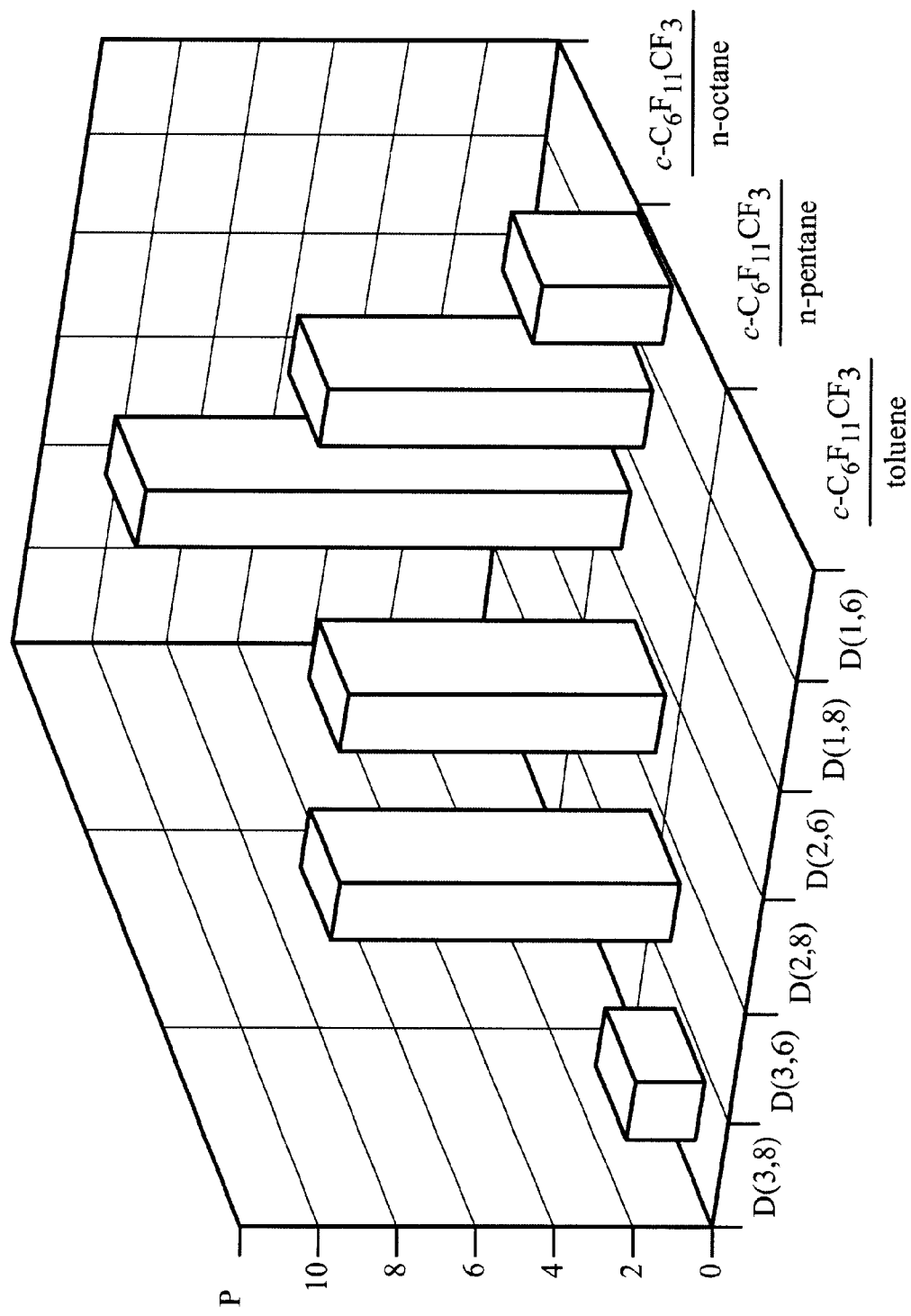
FIG. 4. Partitioning coefficients P for phosphines D{m,x} in several fluorous biphasic solvent systems with c-C$_6$F$_{11}$CF$_3$ as the fluorous phase. The invention will now be further illustrated by the following examples which do not intend to limit the scope of the invention.

It is certified that error appears in the above-identified patent and that said Letters Patent is hereby corrected as shown below:

<u>Drawings,</u>
Substitute Figure 4 (Sheet 4 of 6) with the following:

FIG. 4

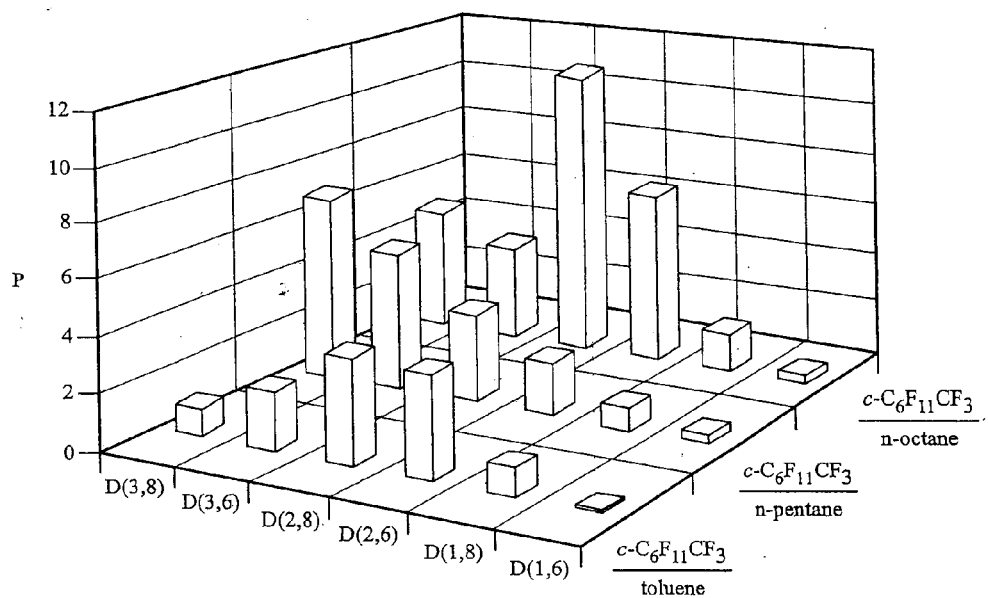

Signed and Sealed this

Ninth Day of May, 2006

JON W. DUDAS
*Director of the United States Patent and Trademark Office*